US011213824B2

(12) United States Patent
Brouzes et al.

(10) Patent No.: US 11,213,824 B2
(45) Date of Patent: Jan. 4, 2022

(54) MICROFLUIDIC DEVICE AND METHODS

(71) Applicant: THE RESEARCH FOUNDATION FOR THE STATE UNIVERSITY OF NEW YORK, Albany, NY (US)

(72) Inventors: Eric Brouzes, Albany, NY (US); Martin Sauzade, Albany, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 100 days.

(21) Appl. No.: 16/495,972

(22) PCT Filed: Mar. 29, 2018

(86) PCT No.: PCT/US2018/025248
§ 371 (c)(1),
(2) Date: Sep. 20, 2019

(87) PCT Pub. No.: WO2018/183744
PCT Pub. Date: Oct. 4, 2018

(65) Prior Publication Data
US 2020/0094251 A1    Mar. 26, 2020

Related U.S. Application Data

(60) Provisional application No. 62/484,451, filed on Apr. 12, 2017, provisional application No. 62/478,289, filed on Mar. 29, 2017.

(51) Int. Cl.
*B01L 3/00*    (2006.01)
(52) U.S. Cl.
CPC ... *B01L 3/502761* (2013.01); *B01L 3/502715* (2013.01); *B01L 3/502784* (2013.01);
(Continued)

(58) Field of Classification Search
CPC ........ B01L 3/502761; B01L 3/502715; B01L 3/502784; B01L 3/50273;
(Continued)

(56) References Cited

U.S. PATENT DOCUMENTS 7,214,348 B2    5/2007  Desmond et al.
7,270,786 B2    9/2007  Parunak et al.
(Continued)

FOREIGN PATENT DOCUMENTS

CN    111133314 B    5/2020
CN    106552682 B    6/2020
(Continued)

OTHER PUBLICATIONS

International Search Report dated Jun. 20, 2018 issued in PCT/US2018/025248.
(Continued)

*Primary Examiner* — Jennifer Wecker
*Assistant Examiner* — Kathryn Elizabeth Limbaugh
(74) *Attorney, Agent, or Firm* — Scully, Scott, Murphy & Presser, P.C.

(57) ABSTRACT

This disclosure provides devices and methods for the isolation of single cells or particles of interest from a solution comprising a plurality of cells or a solution composed of a homogenous population of particles. Specifically, the present disclosure is directed to microfluidic devices and methods for analyzing cells in a sample. More specifically, the present disclosure provides droplet microfluidic devices and methods for using the same to obtain (trap), encapsulate, and retrieve (isolate) single cells or particles from a sample with improved efficiency.

19 Claims, 17 Drawing Sheets

(52) U.S. Cl.
CPC ... *B01L 3/50273* (2013.01); *B01L 2200/0668* (2013.01); *B01L 2300/0816* (2013.01); *B01L 2300/0864* (2013.01); *B01L 2300/0867* (2013.01); *B01L 2400/0487* (2013.01)

(58) Field of Classification Search
CPC ..... B01L 2200/0668; B01L 2300/0816; B01L 2300/0864; B01L 2300/0867; B01L 2400/0487
See application file for complete search history.

(56) References Cited

U.S. PATENT DOCUMENTS

| | | |
|---|---|---|
| 7,312,085 B2 | 12/2007 | Chou et al. |
| 7,323,140 B2 | 1/2008 | Handique et al. |
| 7,472,794 B2 | 1/2009 | Oakey et al. |
| 7,731,906 B2 | 6/2010 | Handique et al. |
| 7,745,211 B2 | 6/2010 | Takayama et al. |
| 8,353,682 B2 | 1/2013 | Patrascu et al. |
| 8,475,743 B2 | 7/2013 | Facer et al. |
| 8,557,518 B2 | 10/2013 | Jovanovich et al. |
| 8,592,221 B2 | 11/2013 | Fraden et al. |
| 8,617,488 B2 | 12/2013 | Woudenberg et al. |
| 8,658,418 B2 | 2/2014 | Daridon |
| 8,772,046 B2 | 7/2014 | Fraden et al. |
| 8,815,177 B2 | 8/2014 | Perroud et al. |
| 8,906,669 B2 | 12/2014 | Dimov et al. |
| 8,992,858 B2 | 3/2015 | Chou et al. |
| 9,121,058 B2 | 9/2015 | Stern et al. |
| 9,138,700 B2 | 9/2015 | VanDam et al. |
| 9,168,521 B2 | 10/2015 | Delamarche et al. |
| 9,174,212 B2 | 11/2015 | Huang |
| 9,201,060 B2 | 12/2015 | Voldman et al. |
| 9,216,412 B2 | 12/2015 | Putnam et al. |
| 9,304,065 B2 | 4/2016 | Fowler et al. |
| 9,354,156 B2 | 5/2016 | Lee et al. |
| 9,500,645 B2 | 11/2016 | Putnam et al. |
| 9,744,533 B2 | 8/2017 | Breinlinger et al. |
| 9,759,718 B2 | 9/2017 | Putnam et al. |
| 9,808,798 B2 | 11/2017 | Ismagilov et al. |
| 9,822,356 B2 | 11/2017 | Ismagilov et al. |
| 9,822,890 B2 | 11/2017 | Juncker et al. |
| 9,952,126 B2 | 4/2018 | Fowler et al. |
| 9,995,668 B2 | 6/2018 | Renaud et al. |
| 9,999,883 B2 | 6/2018 | Taylor et al. |
| 10,052,631 B2 | 8/2018 | Ben-Yakar et al. |
| 10,159,978 B2 | 12/2018 | Linder et al. |
| 10,162,162 B2 | 12/2018 | Wang et al. |
| 10,202,577 B2 | 2/2019 | Spuhler et al. |
| 10,330,643 B2 | 6/2019 | Rivas et al. |
| 10,357,772 B2 | 7/2019 | Fraden et al. |
| 10,501,789 B2 | 12/2019 | Baroud et al. |
| 10,583,439 B2 | 3/2020 | Koksal et al. |
| 10,632,465 B2 | 4/2020 | Dangla et al. |
| 10,689,608 B2 | 6/2020 | Levner et al. |
| 10,829,728 B2 | 11/2020 | Kurz et al. |
| 10,946,133 B2 | 3/2021 | Fiering et al. |
| 10,962,527 B2 | 3/2021 | Blainey et al. |
| 11,001,896 B2 | 5/2021 | Abate et al. |
| 11,022,603 B2 | 6/2021 | Beckwith et al. |
| 11,066,699 B2 | 7/2021 | Baroud et al. |
| 2002/0197167 A1 | 12/2002 | Kornelsen |
| 2003/0061687 A1 | 4/2003 | Hansen et al. |
| 2004/0018116 A1 | 1/2004 | Desmond et al. |
| 2007/0099289 A1 | 5/2007 | Irimia et al. |
| 2007/0134807 A1 | 6/2007 | Bao et al. |
| 2008/0020368 A1 | 1/2008 | Yang et al. |
| 2008/0067068 A1 | 3/2008 | Li |
| 2008/0223721 A1 | 9/2008 | Cohen et al. |
| 2009/0008253 A1 | 1/2009 | Gilbert et al. |
| 2009/0257920 A1 | 10/2009 | Facer et al. |
| 2009/0305901 A1 | 12/2009 | Seemann et al. |
| 2010/0137163 A1 | 6/2010 | Link et al. |
| 2011/0030808 A1 | 2/2011 | Chion et al. |
| 2011/0081275 A1 | 4/2011 | Claussen et al. |
| 2011/0086352 A1 | 4/2011 | Bashir et al. |
| 2012/0129719 A1 | 5/2012 | Quake et al. |
| 2012/0195810 A1 | 8/2012 | Cohen et al. |
| 2012/0207654 A1 | 8/2012 | Lee et al. |
| 2012/0244043 A1 | 9/2012 | Leblanc et al. |
| 2012/0276543 A1 | 11/2012 | Quake et al. |
| 2012/0298233 A1 | 11/2012 | Rothacher |
| 2013/0078163 A1 | 3/2013 | Chung et al. |
| 2013/0186433 A1 | 7/2013 | Wang et al. |
| 2013/0217583 A1 | 8/2013 | Link et al. |
| 2013/0224736 A1 | 8/2013 | Marie et al. |
| 2013/0302884 A1 | 11/2013 | Fowler et al. |
| 2013/0337500 A1 | 12/2013 | Tan et al. |
| 2014/0115606 A1 | 4/2014 | Hamzata et al. |
| 2014/0208832 A1 | 7/2014 | Hansen et al. |
| 2014/0318645 A1 | 10/2014 | Koksal et al. |
| 2015/0018226 A1 | 1/2015 | Hansen et al. |
| 2015/0024436 A1 | 1/2015 | Eberhart et al. |
| 2015/0083320 A1 | 3/2015 | Putnam |
| 2015/0086424 A1 | 3/2015 | Putnam et al. |
| 2015/0087558 A1 | 3/2015 | Putnam et al. |
| 2015/0087559 A1 | 3/2015 | Putnam et al. |
| 2015/0125865 A1 | 5/2015 | Johnson et al. |
| 2015/0125947 A1 | 5/2015 | Korczyk et al. |
| 2015/0352547 A1 | 12/2015 | Breinlinger et al. |
| 2015/0352552 A1 | 12/2015 | Levenberg et al. |
| 2016/0067711 A1 | 3/2016 | Yoon et al. |
| 2016/0123858 A1 | 5/2016 | Kapur et al. |
| 2016/0175835 A1 | 6/2016 | Taylor et al. |
| 2016/0175836 A1 | 6/2016 | Taylor et al. |
| 2016/0199837 A1 | 7/2016 | Breinlinger et al. |
| 2017/0267968 A1 | 9/2017 | Vanapalli et al. |
| 2017/0312748 A1 | 11/2017 | Cornaglia et al. |
| 2018/0010179 A1 | 1/2018 | Hansen et al. |
| 2018/0037934 A1 | 2/2018 | Polytechnique et al. |
| 2018/0056294 A1 | 3/2018 | Di Carlo et al. |
| 2018/0066248 A1 | 3/2018 | Kusner et al. |
| 2018/0272347 A1 | 9/2018 | Zenhausem et al. |
| 2018/0305682 A1 | 10/2018 | Craighead et al. |
| 2018/0311669 A1 | 11/2018 | Basu et al. |
| 2018/0369818 A1 | 12/2018 | Kiani et al. |
| 2019/0046985 A1 | 2/2019 | Kang et al. |
| 2019/0049434 A1 | 2/2019 | Blainey et al. |
| 2019/0060900 A1 | 2/2019 | Breinlinger et al. |
| 2019/0097257 A1 | 3/2019 | Dutta |
| 2019/0344270 A1 | 11/2019 | Yoon et al. |
| 2020/0001292 A1 | 1/2020 | Sabourin et al. |
| 2020/0009568 A1 | 1/2020 | Van Der Zaag et al. |
| 2020/0094251 A1 | 3/2020 | Brouzes et al. |
| 2020/0114352 A1 | 4/2020 | Anand et al. |
| 2020/0171501 A1 | 6/2020 | McEwen et al. |
| 2020/0216791 A1 | 7/2020 | Hansen et al. |
| 2020/0246798 A1 | 8/2020 | Van Der Zaag et al. |
| 2020/0282397 A1 | 9/2020 | Kleine-Bruggeney et al. |
| 2020/0316598 A1 | 10/2020 | Craighead et al. |
| 2020/0316601 A1 | 10/2020 | Dubay et al. |
| 2020/0338552 A1 | 10/2020 | Scherr et al. |
| 2021/0187508 A1 | 6/2021 | Scherr et al. |
| 2021/0221676 A1 | 7/2021 | Han et al. |
| 2021/0262020 A1 | 8/2021 | Link |
| 2021/0277455 A1 | 9/2021 | Sarkar et al. |

FOREIGN PATENT DOCUMENTS

| | | |
|---|---|---|
| CN | 111454831 A | 7/2020 |
| CN | 112566722 A | 3/2021 |
| CN | 113019212 A | 6/2021 |
| DE | 11 2010 005 887 T5 | 9/2013 |
| DE | 11 2015 006 185 T5 | 10/2017 |
| EP | 1 525 919 A1 | 4/2005 |
| EP | 2 071 189 A1 | 6/2009 |
| EP | 2 286 125 B1 | 7/2015 |
| EP | 3 142 790 B1 | 3/2019 |
| EP | 3 401 014 B1 | 7/2020 |
| JP | 2993982 B2 | 12/1999 |
| JP | 2001-515216 A | 9/2001 |
| JP | 2002-544494 A | 12/2002 |
| JP | 2004-536004 A | 12/2004 |
| JP | 2005-533652 A | 11/2005 |

(56) References Cited

FOREIGN PATENT DOCUMENTS

| | | |
|---|---|---|
| JP | 2006-511762 A | 4/2006 |
| JP | 2006-513857 A | 4/2006 |
| JP | 2009-685 A | 1/2009 |
| JP | 2009-166041 A | 7/2009 |
| JP | 2009-530638 A | 8/2009 |
| JP | 2010-151821 A | 7/2010 |
| JP | 2010-180222 A | 8/2010 |
| JP | 4565026 B2 | 10/2010 |
| JP | 2013-515599 A | 5/2013 |
| JP | 2013-541331 A | 11/2013 |
| JP | 2015-510111 A | 4/2015 |
| JP | 2015-515263 A | 5/2015 |
| JP | 2016-523365 A | 8/2016 |
| JP | 2017-500062 A | 1/2017 |
| JP | 6061313 B2 | 1/2017 |
| JP | 6169111 B2 | 7/2017 |
| JP | 6190822 B2 | 8/2017 |
| JP | 2018-525022 A | 9/2018 |
| JP | 6506747 B2 | 4/2019 |
| JP | 6628607 B2 | 1/2020 |
| JP | 2020-536724 A | 12/2020 |
| KR | 10-2010-0028526 A | 3/2010 |
| KR | 10-2011-0111449 A | 10/2011 |
| KR | 10-2013-0099122 A | 9/2013 |
| KR | 10-1506936 B1 | 3/2015 |
| KR | 10-2018-0062936 A | 6/2018 |
| KR | 10-1936842 B1 | 1/2019 |
| KR | 10-2019-0031516 A | 3/2019 |
| KR | 10-2070469 B1 | 1/2020 |
| KR | 10-2020-0012020 A | 2/2020 |
| KR | 10-2020-0067842 A | 6/2020 |
| KR | 10-2020-0070372 A | 6/2020 |
| WO | 2007/133710 A2 | 11/2007 |
| WO | 2008/130623 A1 | 10/2008 |
| WO | 2009/092106 A1 | 7/2009 |
| WO | 2013/142847 A1 | 9/2013 |
| WO | 2014/085801 A1 | 6/2014 |
| WO | 2014/165559 A2 | 10/2014 |
| WO | 2015/188171 A1 | 12/2015 |
| WO | 2016/078339 A1 | 5/2016 |
| WO | 2018/075577 A1 | 4/2018 |
| WO | 2018/100421 A1 | 6/2018 |
| WO | 2018/191534 A1 | 10/2018 |
| WO | 2019/079714 A1 | 4/2019 |
| WO | 2019/091145 A1 | 5/2019 |
| WO | 2020/057531 A1 | 3/2020 |
| WO | 2020/109379 A1 | 6/2020 |
| WO | 2020/176882 A1 | 9/2020 |
| WO | 2020/200351 A1 | 10/2020 |
| WO | 2021/077230 A1 | 4/2021 |
| WO | 2021/103970 A1 | 6/2021 |
| WO | 2021/146350 A2 | 7/2021 |
| WO | 2021/209491 A1 | 10/2021 |

OTHER PUBLICATIONS

Shields, C. Wyatt et al., "Microfluidic Cell Sorting: A Review of the Advances in the Separation of Cells from Debulking to Rare Cell Isolation", Lab Chip (Feb. 16, 2015), vol. 15, No. 5, pp. 1230-1249.

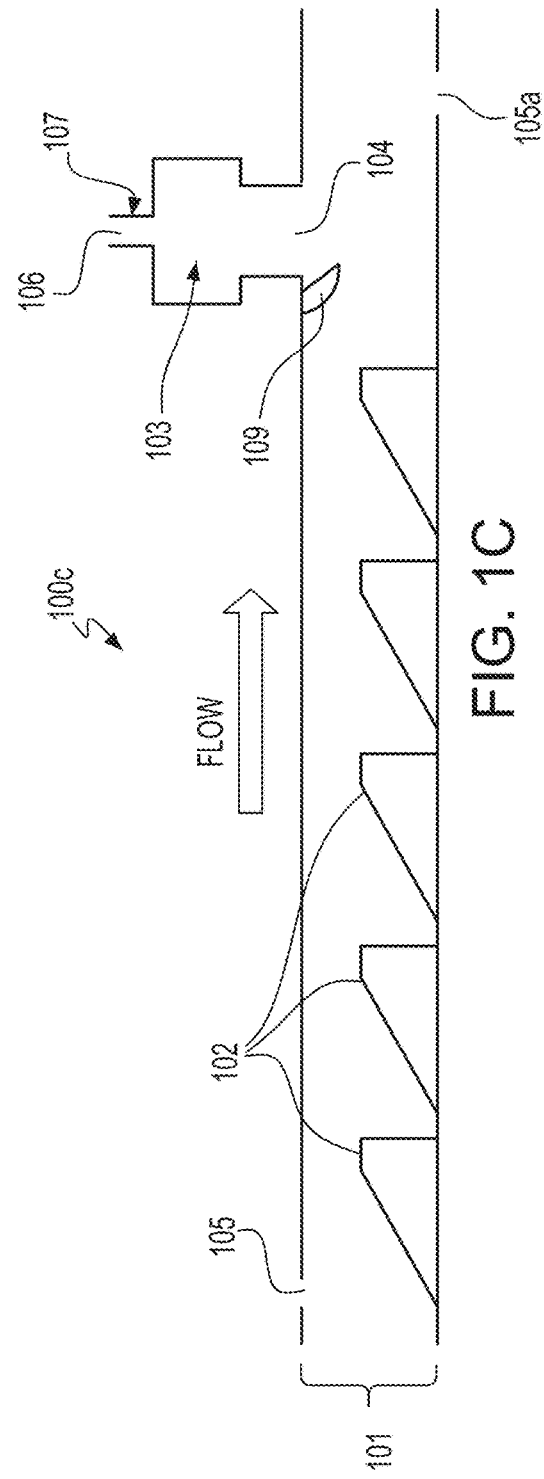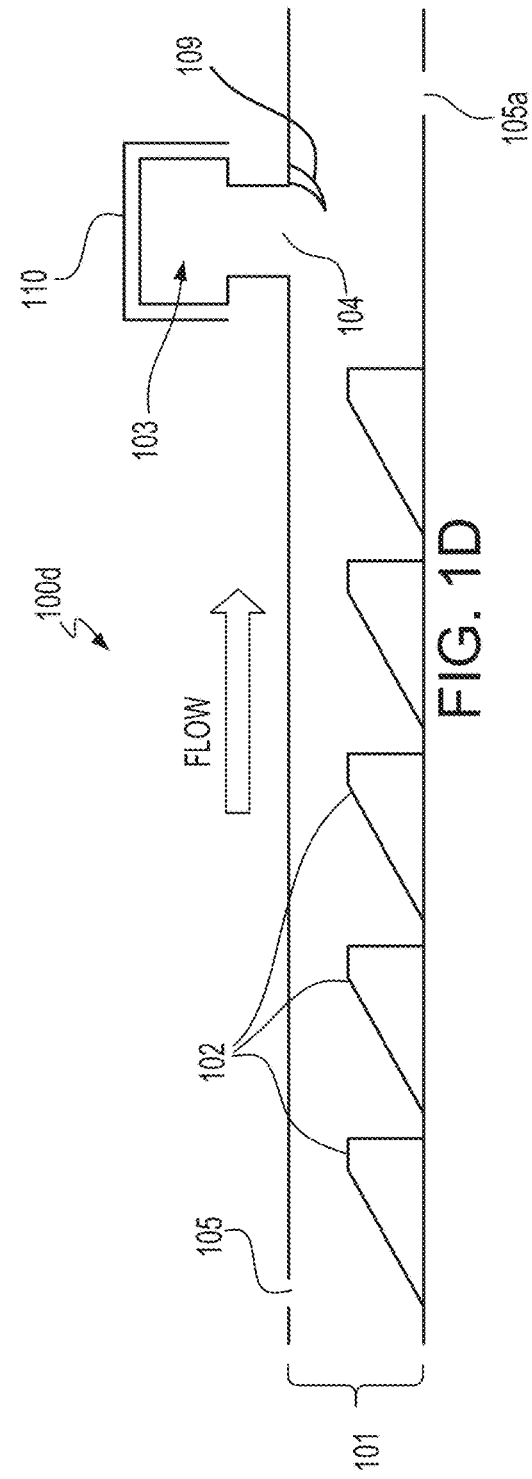

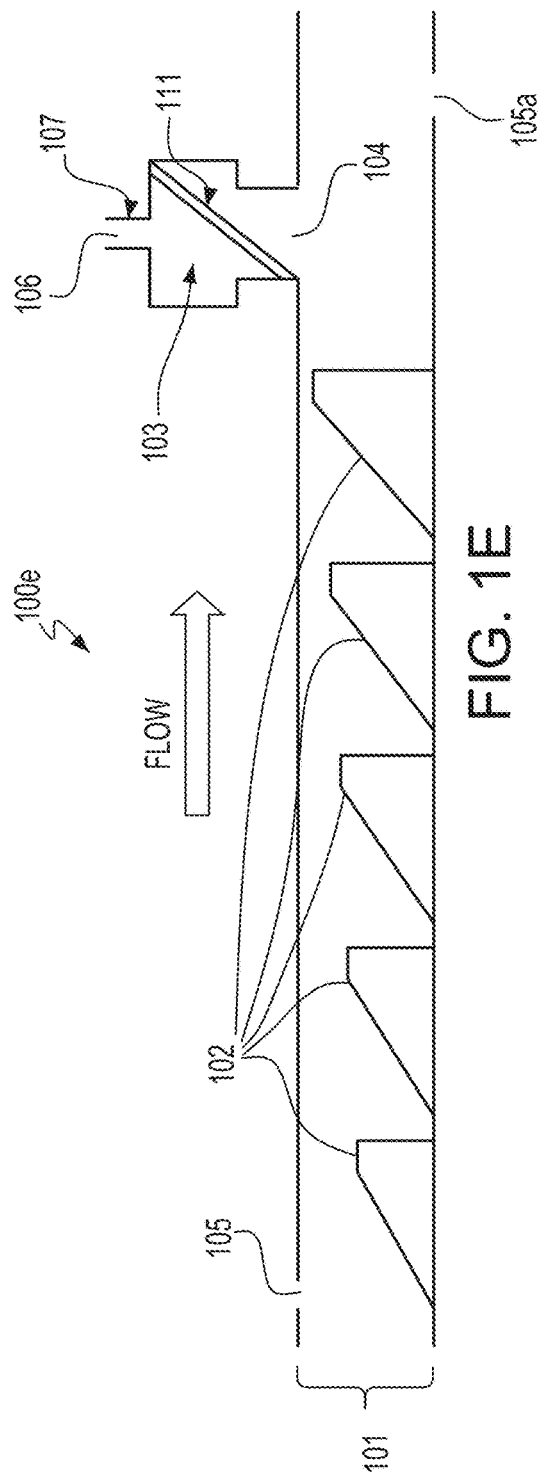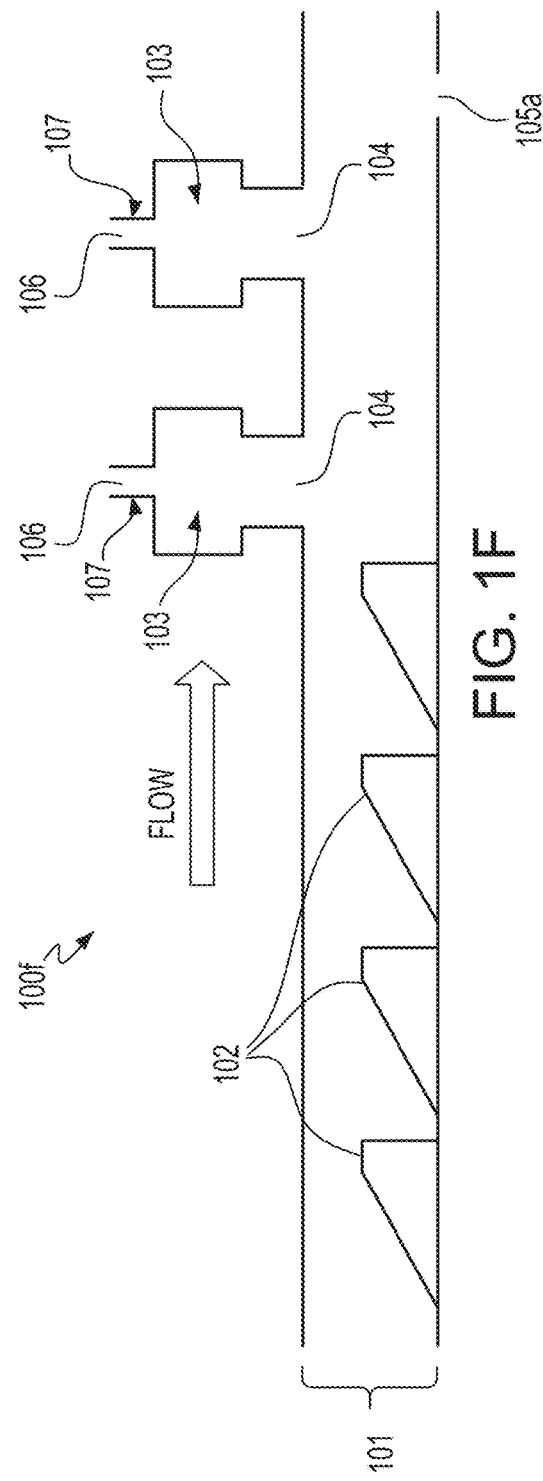

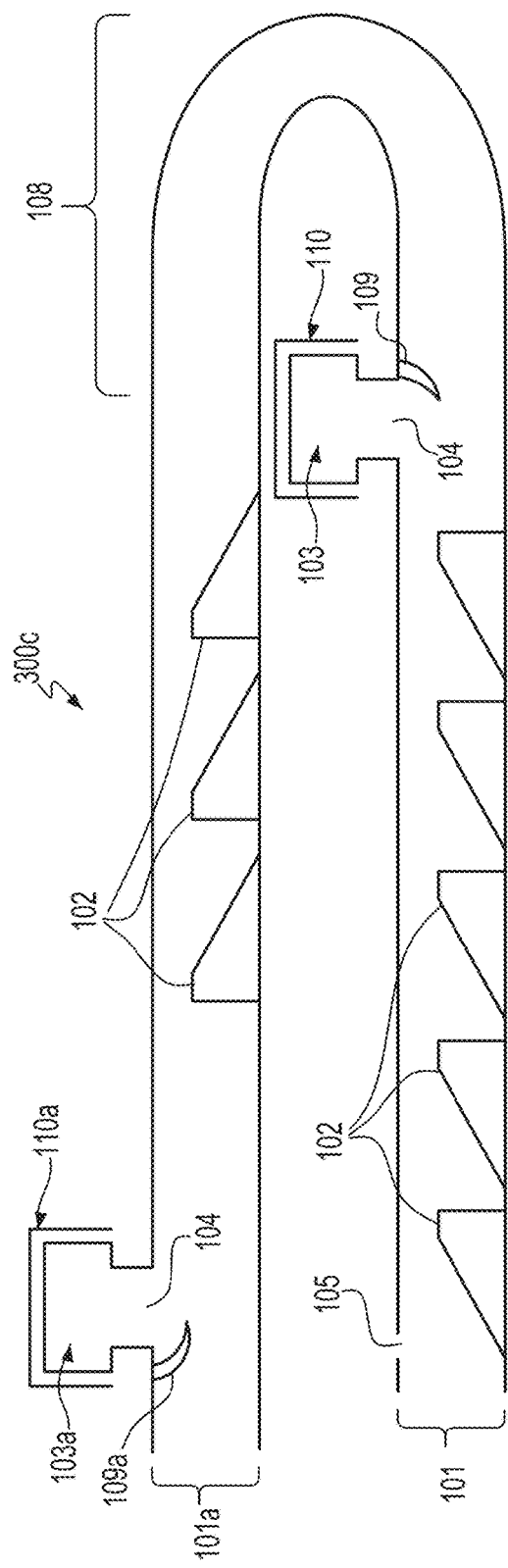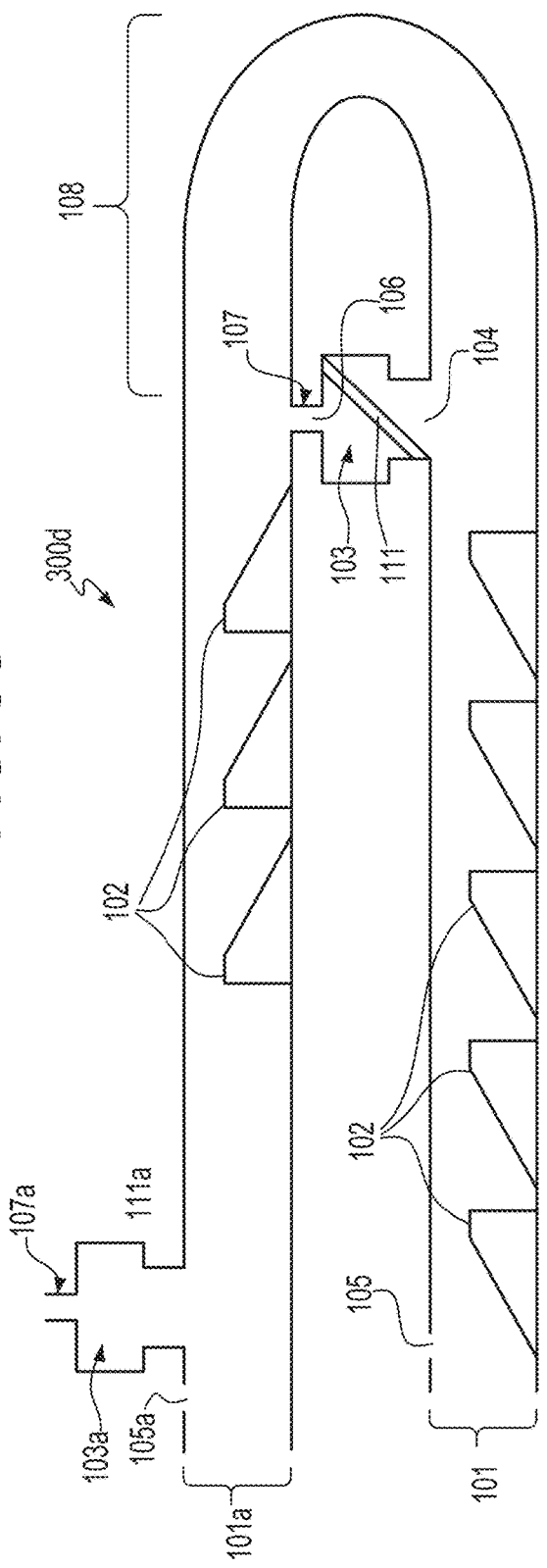

MICROFLUIDIC DEVICE AND METHODS

CROSS REFERENCE TO RELATED APPLICATIONS

This application claims priority from U.S. Provisional Application No. 62/478,289 filed Mar. 29, 2017 and U.S. Provisional Application No. 62/484,451 filed on Apr. 12, 2017 the entire contents of both of which are incorporated herein by reference.

STATEMENT REGARDING FEDERALLY SPONSORED RESEARCH

This invention was made with government support under grant number CA 181595 awarded by the National Institutes of Health. The government has certain rights in the invention.

FIELD OF THE DISCLOSURE

This disclosure relates generally to devices and methods for the isolation of cells or particles of interest. Specifically, the present disclosure is directed to microfluidic devices and methods for analyzing cells or particles in a sample. More specifically, the present disclosure provides a droplet microfluidic device and methods for using the same to obtain (trap), encapsulate, and retrieve (isolate) single cells or particles from a sample with improved efficiency.

BACKGROUND OF THE DISCLOSURE

Microfluidic devices and methods provide researches with multiplexing capabilities, tight control of experimental conditions and require limited sample size (e.g., volume) to obtain valuable data. See Lindstrom, S and Andersson-Svahn, H. *Lab Chip,* 2010, 10 pp. 3363-3372, and Reece, A et al. *Curr. Opin. Biotechnol.,* 2016, 40 pp. 90-96.

Using some microfluidic methods, cells or cellular materials can be made to reside within individual liquid droplets, i.e., droplet microfluidics. Current approaches make use of droplet microfluidics to isolate small amounts of a sample in aqueous droplets surrounded by immiscible oil. See, e.g., Wen, N. et al. *Molecules,* 2016, 21 p. 881 and Klein, A. M., et al. *Cell,* 2015, 161 p. 1187-1201. This can permit cells or other cellular-molecules to be separated, and processed at high-throughput.

Existing processes permit a high number of cells to be encapsulated at high-throughput using microfluidic droplet generators. However, cell distribution within such droplets is random, as the distribution of cells in each droplet is dictated by Poisson statistics. As a result, only 15.6% of all droplets will contain one cell. Tan et al., *J. Am. Chem. Soc.,* 2006, 128 pp. 5656-5658. In order to overcome this deficiency, researchers have attempted to increase flow rate, alter droplet volume and hydrodynamic sorting. See, e.g., Yin, T Y et al., *Biosense. Biolectron.,* 2015, 66 pp. 19-13; and Viovy, J L and Chambert, M., *Proc. Natl. Acad. Sci. U.S.A.,* 2008, 105, pp 3191-3196. However these techniques are marred by substantial cost and device requirements and the need to pre-label cells.

Therefore, there is a need for new droplet microfluidic devices and methods for isolating single cells or particles from a sample at high-efficiency.

SUMMARY OF THE DISCLOSURE

The present disclosure provides unique droplet microfluidic devices and methods to sequentially capture and encapsulate single cells or particles in a microfluidic device. The present devices and methods utilize a trapping scheme that improves single cell or particle capture efficiency and is compatible with single cell or particle encapsulation within individual droplets and retrieval of the same. The microfluidic devices of the present disclosure are compatible with several methods for encapsulation, which provide a fully integrated multi-parameter platform for the analysis of single cells or particles.

Therefore, in a first aspect of present disclosure a microfluidic device is provided that is configured to separate (trap), encapsulate, and optionally retrieve (isolate) single cells or particles from a sample composed of a plurality of cells or a sample composed of a homogenous mixture of particles. The microfluidic device of the present disclosure includes a microfluidic channel having at least one displacement element on a first surface of the microfluidic channel and at least one trapping chamber downstream of the at least one displacement element having a first opening, such that the opening permits the flow of fluid and/or material from the microfluidic channel into the trapping chamber.

In some embodiments, the microfluidic channel includes at least two, at least 3, at least 4, at least 5, at least 6, at least 7, at least 8, at least 9 or more displacement elements aligned in series on a first sidewall surface of the fluid channel, such that each displacement element extends into the microfluidic channel towards the opposite sidewall of the channel. In certain embodiments, the microfluidic channel includes between 3 and 9 displacement elements, between 3 and 7 displacement elements or between 3 and 6 displacement elements, inclusive. In one instance, the microfluidic channel includes 6 displacement elements.

In some embodiments, the displacement elements are each tapered having a maximum height extending toward the opposing sidewall of the fluid channel into the fluid channel, and a width that progressively decreases as the displacement element extends into the fluid channel, i.e., tapered. In certain embodiments, the maximum height of a displacement element is between 10 µm and 40 µm, 14 µm and 40 µm, between 14 µm and 30 µm, between 14 µm and 25 µm, between 14 µm and 20 µm, 10 µm and 27 µm, between 10 µm and 26 µm, between 10 µm and 25 µm, between 15 µm and 25 µm, between 17 µm and 23 µm, or between 18 µm and 22 µm. In other embodiments, the displacement elements have a maximum height extending into the channel defined by the distance between the topmost surface of the displacement element and the opposing wall of the fluid channel that is less than 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, or 30 µm.

In some embodiments, each of the at least one the displacement elements have uniform dimensions. In other embodiments, each displacement element in a plurality of displacement elements extend the same distance into the fluid channel towards the opposite sidewall of the fluid channel. In other instances, each of the displacement elements in a plurality of displacement elements, from start to finish, extends a distance greater toward the opposite sidewall of the fluid channel than the preceding displacement element in the plurality of displacement elements.

In certain embodiments, each of the at least one displacement elements are located downstream of a port in the microfluidic channel. In some embodiments, each of the at least one displacement elements are located in the microfluidic channel between an input port and a trapping chamber. In some embodiments, the input port is located upstream of the at least one displacement element. In other embodiments, each of the at least one displacement elements are located between two ports in a sidewall of the microfluidic channel. Here, the microfluidic device includes a first port by which a solution can be injected into the microfluidic channel (i.e., an input port) and another port from which solution and/or an encapsulated cell exits the microfluidic channel (i.e., an output port). In one embodiment, the retrieval port is located downstream of the at least one displacement element. In other embodiments, the retrieval port is located downstream of the at least one trapping chamber. In yet another embodiment, the retrieval port is located upstream of the at least one displacement element.

The microfluidic device of the present disclosure includes at least one trapping chamber located downstream of the at least one displacement element. Here, the trapping chamber(s) are configured to trap a single cell present in a sample (e.g., solution) after the cell has passed at least a portion of the at least one displacement elements. A trapping chamber has a first opening that permits the flow of fluid and/or material from the microfluidic channel into trapping chamber.

In some embodiments, the trapping chamber has sidewalls extending in a direction away from the microfluidic channel and the first opening and another sidewall connecting the sidewalls extending away from the first opening to form an enclosed chamber. In certain embodiments, the sidewalls extending away from the first opening are parallel to each other. In other embodiments, the sidewalls extending away from the first opening and microfluidic channel are not parallel. For example, the trapping chamber can be a U-shaped enclosure, have one or more tapered sides or have an amorphous shape. In one embodiment, each of the at least one trapping chambers have the same dimensions. In another embodiment, one or more of the at least one trapping chambers have different dimensions. In yet another embodiment, each of the at least one trapping chambers have different dimensions.

In some embodiments, the trapping chamber is fully enclosed except for the first opening. In one embodiment the trapping chamber is at least partially surrounded by a pressurized channel capable of compressing the outer sidewalls of the trapping chamber.

In other embodiments, a trapping chamber has a second opening at the opposite end of the chamber from the first opening through which fluid can flow. Here, fluid will flow into the trapping chamber from microfluidic channel through the first opening, traverse the trapping chamber and flow through the second opening into a channel, i.e., a trapping channel. As such, in some embodiments, the second opening in the trapping chamber is connected to another microfluidic channel by a trapping channel.

In some instances, the second opening is smaller than the first opening. In some embodiments, the first opening has a width and height that permits the passage of fluid that includes at least one cell, and the second opening has a width and height that permits the passage of fluid but not a cell or particle of interest. In a specific embodiment, the second opening has a width that is narrower than the diameter of a cell or particle of interest. In one embodiment, the second opening has a width that is narrower than the diameter of a cell or particle of interest, but a height that is greater than the total height of the cell or particle of interest, so as to prevent passage of the cell or particle of interest through the second opening but permit the flow of fluid through the second opening. In one embodiment, the second opening has a height that is lesser than the total height of a cell or particle of interest, but a width that is greater than the diameter of the cell or particle of interest, so as to prevent passage of the cell or particle of interest through the second opening but permit the flow of fluid through the second opening. In some embodiments the second opening has a cross-sectional diameter that is smaller than that of a cell or particle of interest or identical to that of a cell of interest or particle of interest.

In some embodiments, the microfluidic device of the present disclosure includes a capture element, whereby the capture element protrudes into the first opening of a trapping chamber. In certain embodiments, the capture element can be hook-shaped. In one embodiment, the capture element can be a hook that protrudes into the first opening of the trapping chamber and into a portion of the channel. In some embodiments, the capture element can be positioned downstream of the trapping chamber. In other embodiments, the capture element can be positioned upstream of the trapping chamber.

In certain instances, the microfluidic device of the present disclosure includes a blocking rail that traverses an inner portion of the trapping chamber. Here, the blocking rail will be affixed to the inner sidewalls of a trapping chamber and positioned such that the blocking rail will trap a passing cell in a "pocket" within the trapping chamber, but will permit the flow of fluid over and/or under the blocking rail.

In one embodiment, the microfluidic device of the present disclosure includes a pressurized control channel. Here, the pressurized control channel overlies the outermost surface of a trapping chamber. In some instances, the pressurized control channel is maintained at atmospheric pressure or below. Here it will be readily known by those of ordinary skill in the art, that atmospheric pressure is equal to about 101 325 Pa, 760 mmHg and 14.696 psi. For example, the pressurized control channel can be maintained at 0.1 atmospheres (atm) to 1.0 atm, 0.2 atm to 1.0 atm, 0.3 atm to 1.0 atm, 0.4 atm to 1.0 atm, 0.5 atm to 1.0 atm, 0.6 atm to 1.0 atm, 0.7 atm to 1.0 atm, 0.8 atm to 1.0 atm, or 0.9 atm to 1.0 atm. In other instances, a positive pressure is applied to the pressurized control channel such that the underlying trapping chamber is compressed. In this embodiment, the pressure in the trapping chamber is greater than 1.0 atm, between 1.0 atm and 2.0 atm, or between 1.5 atm, and 2 atm, or higher. However, any pressure can be applied that is sufficient to compress the underlying trapping chamber, which can readily be determined by one of ordinary skill in the art.

In some instances, the microfluidic device of the present disclosure includes at least two microfluidic channels that are adjoined by a bypass channel. Here, the bypass channel is located downstream of the at least one trapping chamber such that the bypass chamber connects two adjacent microfluidic channels forming a pathway through which fluid can flow. In certain embodiments, the bypass channel is curved, such as for example, U-shaped. In one embodiment, the bypass channel has the same diameter as the microfluidic channel. In other embodiments, the bypass channel is narrower, or wider than the microfluidic channel. In such an embodiment, the microfluidic device can include one or more trapping chambers affixed to a trapping channel that connects the trapping chamber(s) of one microfluidic channel to an adjacent microfluidic channel.

In certain embodiments, the microfluidic device of the present disclosure includes 2, 3, 4, 5, 6 or more microfluidic channels arranged in fluid communication with one another, such that a bypass channel connects two adjacent microfluidic channels to form a microfluidic circuit.

The microfluidic devices of the present disclosure facilitate the efficient trapping and encapsulation of single cells or particles from a sample in microfluidic droplets. As such, the present disclosure also provides methods for encapsulating single cells or particles from a sample using the microfluidic device described above.

In one aspect of the present disclosure, a method for encapsulating single cells or particles of interest includes providing a first solution having at least one cell or particle of interest into a microfluidic channel of the device at a position upstream of the at least one displacement element. Here, a positive pressure is applied to the microfluidic channel maintaining a desired rate of flow for the first solution through the microfluidic device forcing the at least one cell through the microfluidic channel past the at least one displacement element, which direct the flow of the at least one cell to the first opening in the trapping chamber.

In one embodiment, a positive pressure is applied to the microfluidic channel maintaining a desired rate of flow for the first solution through the microfluidic device forcing the at least one particle of interest through the microfluidic channel past the at least one displacement element, which direct the flow of the at least one particle of interest to the first opening in the trapping chamber.

The first solution can be an aqueous solution that includes one or more cells, a buffer reagent and/or dissolved ions. The cell may be trapped by the first trapping chamber, or, the cell may be trapped by a subsequent trapping chamber in the series of channels. The cell remains in the trapping chamber while the first solution continues to flow through the channel. The cell may be trapped by any of the foregoing microfluidic devices.

The first solution can be an aqueous solution that includes a homogenous population of one or more particles of interest, a buffer reagent and/or dissolved ions. The particle of interest may be trapped by the first trapping chamber, or, the particle may be trapped by a subsequent trapping chamber in the series of channels. The particle remains in the trapping chamber while the first solution continues to flow through the channel. The particle may be trapped by any of the foregoing microfluidic devices.

A second immiscible solution is then injected into a port and a pressure is applied to said second solution that directs the flow rate of the solution through the microfluidic device forming one or more interfaces with the first solution. In some embodiments the second solution flows in a direction opposite to that of the first solution. In other embodiments the second solution flows in the same direction as the first solution.

In some embodiments, the second solution encapsulates a trapped cell in the first solution by removing a trapped cell or particle of interest from a trapping channel. In other embodiments, the second solution encapsulates a trapped cell or particle of interest in the first solution by surrounding said trapped cell or particle of interest in a portion of said trapping chamber.

In some embodiments, the methods include retrieving a droplet comprising a single-cell or particle of interest from a trapping chamber. In one embodiment, the trapping chamber containing a droplet is compressed to force the droplet out of the first opening of a trapping chamber into a microfluidic channel. In other embodiments, the flow direction of the second solution is reversed causing a pressure change that forces a droplet out of a trapping chamber.

In one embodiment, the droplets are isolated from the device.

BRIEF DESCRIPTION OF THE DRAWINGS

FIGS. 1A-1F: Exemplary microfluidic devices of the present disclosure. FIG. 1A: a vertical cross section of a first exemplary microfluidic device (100a) of the present disclosure having a microfluidic channel (101) that includes a plurality of displacement elements (102) on a first surface of the microfluidic channel, an input port (105) for providing fluid to the microfluidic channel (101), and a trapping chamber (103) having a first opening (104) and a second opening (106) connecting the trapping chamber to a trapping channel (107). In the depicted embodiment, the trapping chamber (103) has a U-shaped portion located downstream of the first and second openings. FIG. 1B: a vertical cross section of another exemplary microfluidic device of the present disclosure (100b) including a microfluidic channel (101) having a plurality of displacement elements (102) within the microfluidic channel (101), a retrieval port (105a) for isolating an encapsulated cell, and a trapping chamber (103) having parallel sidewalls, a first opening (104) and a second opening (106) connecting the trapping chamber to a trapping channel (107). FIG. 1C: a vertical cross section of a third exemplary microfluidic device of the present disclosure (100c) including a microfluidic channel (101) having a plurality of displacement elements (102) within the microfluidic channel (101), an input port (105) for providing fluid to the microfluidic channel (101), a retrieval port (105a) for isolating an encapsulated cell, a capture structure (109) at the first opening (104) of the trapping chamber (103), which has a trapping channel (107) affixed to the opposite side of the trapping chamber (103). FIG. 1D: a vertical cross section of a fourth exemplary microfluidic device of the present disclosure (100d) including a microfluidic channel (101) having a plurality of displacement elements (102) within the microfluidic channel (101), an input port (105), a retrieval port (105a), a hook-shaped capture structure (109) overhanging a portion of a first opening (104) of the trapping chamber (103). In the depicted embodiment the trapping chamber is contacted on at least three sides by a pressurized control element (110). FIG. 1E: a vertical cross section of another exemplary microfluidic device of the present disclosure (100e) including a microfluidic channel (101) having a plurality of displacement elements (102) within the microfluidic channel (101), an input port (105) for providing a fluid sample to the microfluidic channel (101), a retrieval port (105a) for isolating an encapsulated cell, a blocking rail (111) that sections off a first portion of the trapping chamber (103). In this embodiment, the trapping chamber (103) includes a trapping channel (107). Here, the depicted microfluidic device (100e) includes a plurality of displacement elements (102), whereby each displacement element (102) increases in height when compared to the preceding displacement element (102). FIG. 1F: In the depicted embodiment, a microfluidic device of the present disclosure has more than one trapping chamber (103). Here, the microfluidic device (100f) includes a fluid channel (101) having a plurality of displacement elements (102) within the microfluidic channel (101), a retrieval port (105a) for isolating an encapsulated cell, and multiple trapping chambers (103), each having a first opening (104) and a second opening (106) connecting the trapping chamber to a trapping channel (107).

FIG. 2A: Three-dimensional depiction of exemplary displacement elements (102) shown as a horizontal cross-section. FIG. 2B: The inset dimensions (in micrometers) of the exemplary displacement element shown in FIG. 2A. FIG. 2C: Photography of additional exemplary displacement elements (102) for use in any of the microfluidic devices or methods of the present disclosure. Here, each microfluidic channel used to compare displacement structure function was identical. The displacement elements designated as "v3" have maximum height of 20 µm. Displacement elements designated as "v4" have maximum height of 10 µm, and displacement elements designated as "v5" have maximum height of 30 µm. Liquid was then flowed through each channel from position γi to γf to calculate the displacement of cells over each set of displacement elements tested. The data was then fit with a linear slope, where integration of slope lines provides the displacement coefficient or ability of the exemplary displacement elements to relocate cell flow through the channel. FIG. 2D: A comparison of displacement coefficients for the different displacement elements investigated. FIG. 2E: provides a time lapse of a cell containing solution (fluid sample) flowing from a first end (γi) of the microfluidic channel (101), over the plurality of displacement elements (102) to a second end (γf) of the microfluidic channel (101).

FIGS. 3A-3E: Exemplary microfluidic devices of the present disclosure. FIG. 3A: A vertical cross section of a microfluidic device (300a) of the present disclosure having a first microfluidic channel (101) that includes a plurality of displacement elements (102), an input port (105), and a first trapping chamber (103) having a first opening (104) and a second opening (106) connecting the first trapping chamber (103) to a trapping channel (107). In the depicted microfluidic device (300a), the first microfluidic channel (101) is connected to a second microfluidic channel (101a) having another plurality of displacement elements (102) on a first surface thereof and a second trapping chamber (103a) affixed to a second trapping channel (107a). As shown, the two microfluidic channels (101, 101a) are connected to one another by a bypass channel (108) and by trapping channel (107). FIG. 3B: A vertical cross section of a second microfluidic device (300b) of the present disclosure having a first channel (101) that includes a plurality of displacement elements (102), an input port (105), and a first trapping chamber (103) having a first opening (104) and a second opening (106) connecting the first trapping chamber (103) to a trapping channel (107). In the second microfluidic device (300b), the first microfluidic channel (101) is connected to a second microfluidic channel (101a) having a plurality of displacement elements (102) on a first surface of the second microfluidic channel (101a) and a second trapping chamber (103a) affixed to a second trapping channel (107a). As shown, the two microfluidic channels (101, 101a) are connected to one another by a bypass channel (108) and by a trapping channel (107). In the second microfluidic device each microfluidic channel (101/101a) includes a capture structure (109) at the first opening (104) of each trapping chamber (103/103a). FIG. 3C shows a third exemplary microfluidic element (300c) including a first fluid channel (101) having a plurality of displacement elements (102) within the fluid channel (101), an input port (105), a hook-shaped capture structure (109) overhanging a portion of a first opening (104) of the first trapping chamber (103). In the exemplary microfluidic device (300c), the first microfluidic channel (101) is connected to a second microfluidic channel (101a) having a plurality of displacement elements (102), and a second a hook-shaped capture structure (109a) overhanging a portion of a second opening (104) of the second trapping chamber (103a). As shown, the two microfluidic channels (101, 101a) are connected to one another by a bypass channel (108) and each of the trapping chambers (103/103a) are contacted by a pressurized control element (110/110a). FIG. 3D: shows a vertical cross section of a fourth exemplary microfluidic device (300d) having a first channel (101) that includes a plurality of displacement elements (102), an input port (105), and a first trapping chamber (103) having a first opening (104) and a second opening (106) connecting the first trapping chamber (103) to a trapping channel (107). In the exemplary microfluidic device (300d), the first microfluidic channel (101) is connected to a second microfluidic channel (101a) having a plurality of displacement elements (102) on a first surface of the second microfluidic channel (101a), a retrieval port (105a), and a second trapping chamber (103a) affixed to a second trapping channel (107a). As shown, the two microfluidic channels (101, 101a) are connected by a bypass channel (108) and by trapping channel (107). In this microfluidic device (300d) each trapping chamber (103/103a) includes a blocking rail (111) that sections off a first portion of each trapping chamber (103/103a). FIG. 3E: A vertical cross section of a microfluidic device (300e) of the present disclosure having a first channel (101) that includes a plurality of displacement elements (102), an input port (105), and a first U-shaped trapping chamber (103) having a first opening (104) and a second opening (106) connecting the first U-shaped trapping chamber (103) to a trapping channel (107). In the depicted microfluidic device (300e), the first microfluidic channel (101) is connected to a second microfluidic channel (101a) having a plurality of displacement elements (102) on a first surface of the second microfluidic channel (101a) and a second U-shaped trapping chamber (103a) affixed to a second trapping channel (107a). As shown, the two microfluidic channels (101, 101a) are connected to one another by a bypass channel (108) and by the trapping channel (107).

FIG. 5A: An overlay of a cell or particle flow trajectories showing the impact of the displacement elements on flow path. FIG. 5B: Cells or particles of interest are provided to a microfluidic channel (101) in a first solution and are flowed downstream over a plurality of displacement elements (102) where they are focused toward a trapping chamber (103, 103a, 103b) and are trapped sequentially. FIG. 5C: Cells or particles of interest are provided to a microfluidic channel (101) in a first solution and are flowed downstream over a plurality of displacement elements (not shown) where they are focused toward a trapping chamber (103) having a blocking rail (111) and a second opening (106) that is affixed to a trapping channel (107). A single cell or particle is forced into a "pocket" formed by the blocking rail (111) by the flow and trapped. FIG. 5D: Cells or particles of interest are provided to a microfluidic channel (101) and are flowed downstream over a plurality of displacement elements (not shown) where they are focused toward a trapping chamber (103) having a capture element (109)

located across the first opening (104) of the trapping chamber (103). Here, the trapping chamber also has a second opening (106) that is affixed to a trapping channel (107). A single cell or particle is forced toward the capture element (109) located downstream of the first opening of the trapping chamber where it is captured and remains. FIG. 5E: Cells or particles of interest are provided to a microfluidic channel (101) and are flowed downstream over a plurality of displacement elements (not shown) where they are focused toward a trapping chamber (103) having a capture element (109) located upstream of the first opening (104) of the trapping chamber (103). Again, the trapping chamber also has a second opening (106) that is affixed to a trapping channel (107). A single cell or particle of interest is flowed toward the capture element (109) where it is directed into the trapping chamber (103) and remains trapped due to the flow. FIG. 5F: Cells or particles of interest are provided to a microfluidic channel (101) and are flowed downstream over a plurality of displacement elements (102) where they are focused toward a trapping chamber (103) having a capture element (109) located downstream of the trapping chamber (104). Here, the capture element extends across the first opening (104) of the trapping chamber (103). In this embodiment, the trapping chamber is fully enclosed except for the first opening (103), i.e., it does not have a second opening (106) that is affixed to a trapping channel (107). The trapping chamber is also surrounded by a pressurized trapping channel (110). A single cell or particle of interest is forced toward the capture element (109) located downstream of the first opening of the trapping chamber and directed into the trapping chamber by fluid flow where it remains. Scale bars: 50 μm.

FIG. 6A: A first encapsulation mode, whereby the trapped cell or particle of interest blocks the flow through the trapping channel (107). Here, the second solution (114) (oil) is diverted towards the bypass channel (108) pathway and into the second adjacent microfluidic channel (101a), where it finally surrounds the trapping chamber (103), generating a droplet (115) containing the single trapped cell or particle. FIG. 6B: A second encapsulation method, whereby the second solution (114) is injected at lower flow rates, a thin precursor film of second solution (oil) forms ("wets") ahead of the interface (113), directing the first interface (113) to progresses into the trapping chamber (103) and through the trapping channel (107), releasing the trapped cell or particle into a droplet (115) from within the trapping chamber. FIG. 6C: A third exemplary encapsulation method, utilizing the device of FIG. 3F and the trapping method of FIG. 5B whereby the second opening (106) and/or the trapping channel (107) has a cross-sectional diameter that is not fully blocked by the cell or particle of interest plugged therein. Hence, as the second solution flows downstream toward the trapping chamber (103), the second solution will flow into the trapping chamber (103) and through the trapping channel (107) releasing the cell or particle of interest from the trapping channel (107) and "sweeping" the cell or particle into the trapping chamber (103) where it forms a droplet (115) encapsulating the trapped cell. or particle. FIG. 6D: A fourth exemplary encapsulation method, utilizing the device of FIG. 3D and the trapping method of FIG. 5C whereby the second opening (106) and/or the trapping channel (107) is not blocked by a cell or particle of interest and the cell or particle has been trapped by a blocking rail (111). Hence, as the second solution (114) flows into the trapping chamber (103) around the blocking rail (111) and through the trapping channel (107) forming a droplet (115) within a "pocket" created by the blocking rail (111) that encapsulates the single, trapped cell or particle. FIG. 6E: In another exemplary encapsulation method, when a cell or particle is trapped using the microfluidic device of FIG. 3B and the method set forth in FIG. 5E capillary valving will force the second solution to flow downstream past the trapping channel (107) toward the bypass channel (108). As the second solution flows past the trapping channel (107), the trapped cell or particle will be released from the second opening (106) in the trapping chamber where it was plugged into the trapping chamber where it will be captured by the capture element (109) and retained within the trapping chamber. Then, as the interface (113) progresses into the microfluidic channel toward the first opening (104) in the trapping chamber (103) an interface (113) at the first opening (104) in the trapping chamber (103) is formed, causing a droplet (115) encapsulating the trapped cell or particle to form having the same dimensions of the trapping chamber (103). Scale bar: 50 μm.

DETAILED DESCRIPTION OF THE DISCLOSURE

Figure 1A:
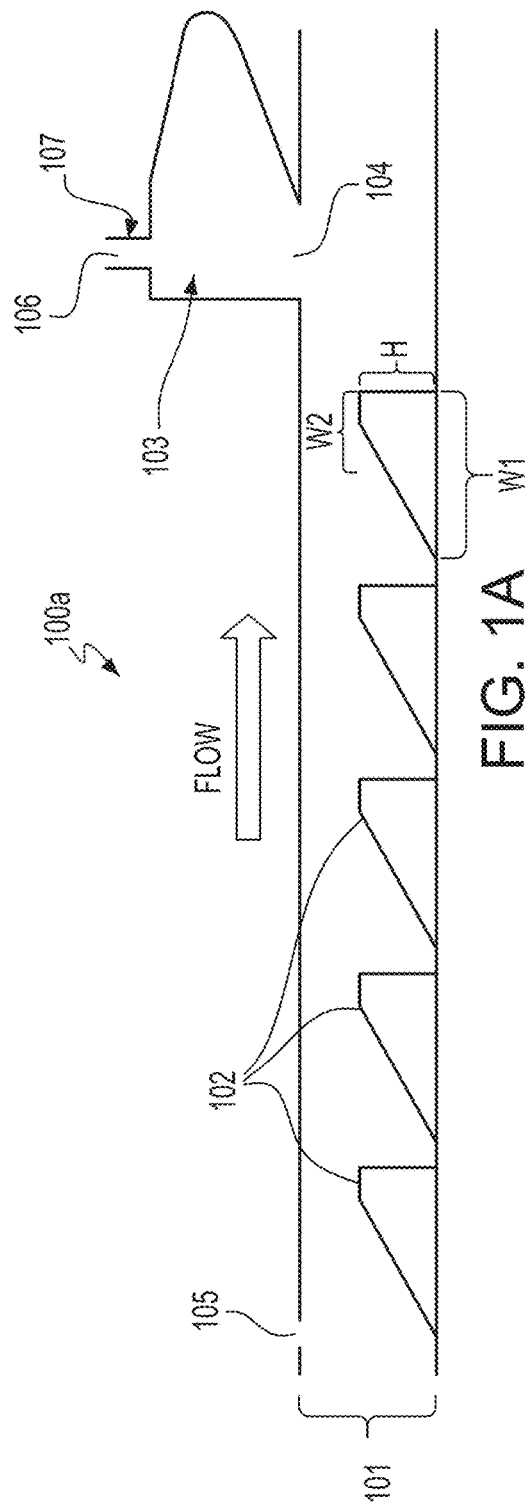
Figure 1B:
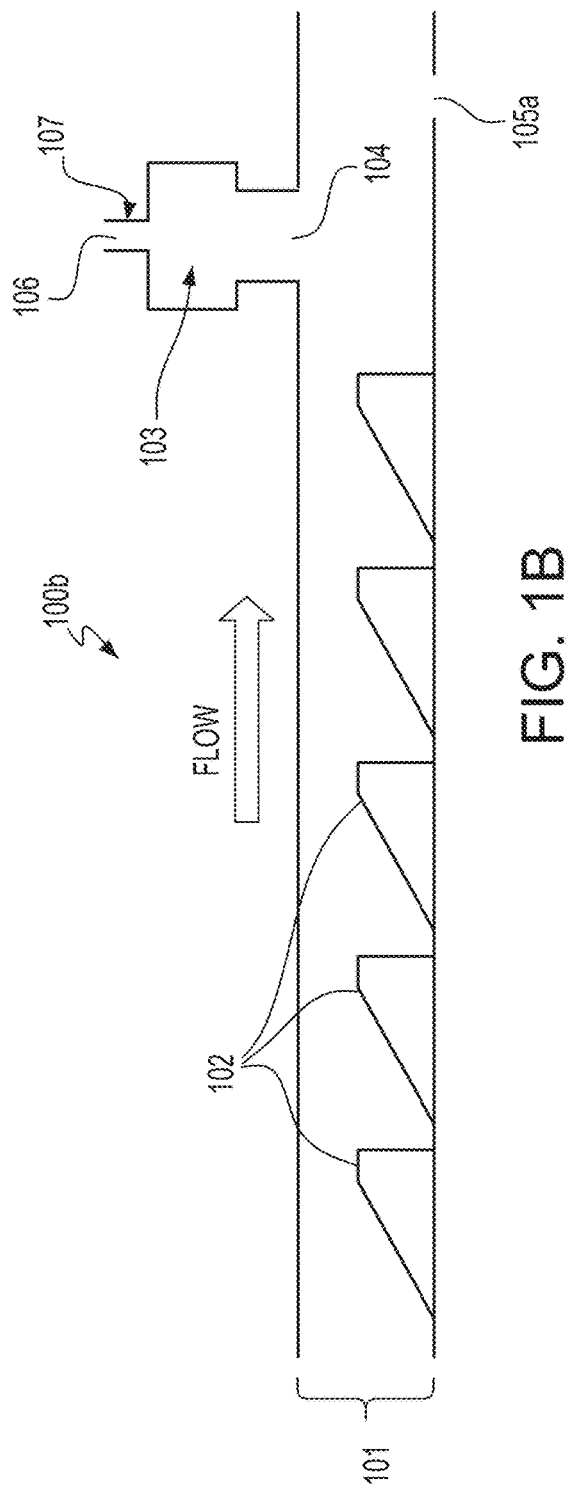

As set forth herein, the microfluidic device and methods of the present disclosure provide a highly efficient single cell or particle of interest trapping and encapsulation.

The terms "a and "an" as used herein unless clearly indicated to the contrary, should be understood to mean one, but also possibly more than one. The term "or", as used herein means inclusively in the alternative.

As used herein, the phrase "at least one" in reference to one or more elements, should be understood to mean at least one element selected from any one or more of the elements in the list of elements, but not necessarily including at least one of each and every element specifically listed within the list of elements and not excluding any combinations of elements in the list of elements. Meaning that elements may optionally be present other than the elements specifically identified within the list of elements that the phrase "at least one" refers to, whether related or unrelated to those elements specifically identified.

References in the specification to "one embodiment", "an embodiment", "an instance", "an example", etc., indicate that the embodiment described may include a particular feature or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. For purposes of the description hereinafter, the terms "upper", "lower", "right", "left", "vertical", "horizontal", "top", "bottom", and derivatives thereof shall relate to the invention, as it is oriented in the drawing figures. The terms "on", "overlying", "atop", "positioned on" or "positioned atop" means that a first element, is present on a second element, wherein intervening elements may interface between the first element and the second element. The term "ajoined", "direct contact", "connected to", "affixed to" or "attached to" means that a first element, and a second element, are connected without any intermediary element at the interface of the two elements.

Devices

In a first aspect of present disclosure, a microfluidic device is provided that is configured to separate (trap), encapsulate, and retrieve (isolate) single cells or particles from a sample composed of a plurality of cells or a sample composed of a homogenous population of particles. As depicted in FIGS. 1A-1F and 3A-3D, the microfluidic device of the present disclosure comprises a first region that includes a microfluidic channel (101) having at least one displacement element (102) on a first surface of the microfluidic channel and at least one trapping chamber (103) downstream of the at least one displacement element (102) having a first opening (104), such that the opening permits the flow of fluid and/or material from the microfluidic channel (101) into the trapping chamber (103).

As used herein, the term "micro" or the "micro-prefix" means an element having widths or diameters of less than about 1 mm, and less than about 100 microns (micrometers). For example, as in "microfluidic device" refers to a device, apparatus or system that includes at least one microscale channel.

A "channel", as used herein, means a feature on or in a device or an element thereof (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of an opening such as, for example a port (inlet or outlet). A channel may have in at least some of its sections an aspect ratio (length to average cross-sectional dimension) of at least 2:1, more typically at least 3:1, 5:1, or 10:1.

As used herein, a "cross-sectional dimension", in reference to a channel, is measured in a direction generally perpendicular to flow of solution within the channel. In some embodiments, the channels (e.g., microfluidic and trapping) of the device may be of a particular size (e.g., the size of a cell or particle of interest), or larger, or smaller.

The elements of the microfluidic device of the present disclosure can be composed of any material known in the art. In some embodiments, the elements of the microfluidic device are composed of a hydrophobic material such as, for example, polydimethylsiloxane (PDMS). In other embodiments, the elements of the microfluidic device are composed of or coated with a hydrophobic material such as, for example, trimethyl-siloxane. For example, a hydrophobic material such as PDMS or tri-methyl-siloxane is used to prevent the fluid (e.g., cell or particle containing solution or immiscible fluid) from adhering to the walls of the microfluidic device (i.e., channel sidewalls, trapping chambers and ports) which could impede one or more of fluid flow, encapsulation, or isolation of an encapsulated cell or particle. By using the natural hydrophobicity of PDMS or other hydrophobic channel coating, the water-cell flow forms an interfacial geometry with the oil phase that is appropriate for droplet formation and the shearing process can be used to create more uniform droplet sizes. In certain embodiments, the elements of the microfluidic device may be composed of a fluorinated thermoplastic (e.g., THV500G (3M™) or THV220 (3M™)).

In certain embodiments, the microfluidic device is composed of polydimethylsiloxane (PDMS). For example, PDMS can be supplied as a mixture of a base and a curing agent, whereby the mixture is introduced on an uppermost surface of a wafer or substrate. The wafer may include pre-fabricated elements (e.g., channels, chambers and openings), which can be formed by etching the wafer or substrate, such as for example by lithographically. Other methods of microfluidic device fabrication known in the art can also be used.

In some embodiments, the microfluidic channel (101) has a cross-sectional depth (from innermost horizontal sidewall to innermost horizontal sidewall) 20 µm to 160 µm with cross-sectional widths (from innermost vertical sidewall to innermost vertical sidewall) of between 20 µm to 80 µm. In other embodiments, the microfluidic channel has width of between 20 µm and 60 µm, 20 µm and 50 µm, 20 µm and 40 µm, or 20 µm and 30 µm.

In a specific embodiment, the microfluidic channel has a cross-sectional width of between 30 µm and 35 µm. In yet other embodiments, the microfluidic channel has width of 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm or 40 µm. In a specific embodiment, microfluidic channel has a width of 32 µm, as depicted in FIG. 2A of the present disclosure.

In some embodiments, the microfluidic channel has cross-sectional depth of between 20 µm and 120 µm, 20 µm and 100 µm, 20 µm and 80, or 20 µm and 60 µm. In a certain embodiments, the microfluidic channel has a depth of between 30 µm and 70 µm, 40 µm and 70 µm, 50 µm and 70 µm, or 40 µm and 60 µm. In a specific embodiment, the microfluidic channel has a depth of between 50 µm and 60 µm. In yet other embodiments, the microfluidic channel has depth of 40 µm, 41 µm, 42 µm, 43 µm, 44 µm, 45 µm, 46 µm, 47 µm, 48 µm, 49 µm, 50 µm, 51 µm, 52 µm, 53 µm, 54 µm, 55 µm, 56 µm, 57 µm, 58 µm, 59 µm, 60 µm, 61 µm, 62 µm, 63 µm, 64 µm, 65 µm, 66 µm, 67 µm, 68 µm, 69 µm or 70 µm. In a specific embodiment, microfluidic channel has a depth of 56 µm, as depicted in FIG. 2A of the present disclosure.

In some instances, the microfluidic channel depth and/or width can be uniform. In other instances, microfluidic channel depth and/or width can be non-uniform.

Further, the microfluidic channels of the present disclosure include at least one displacement elements (102). Here, it has been shown that serial alignment of a plurality of displacement elements in the microfluidic channel can direct flow and steer cells or particles of interest toward a trapping chamber. See FIG. 2D. Therefore, in some embodiments, the microfluidic channel includes at least two, at least 3, at least 4, at least 5, at least 6, at least 7, at least 8, at least 9 or more displacement elements aligned in series on a first sidewall surface of the fluid channel, such that each displacement element extends into the microfluidic channel towards the opposite sidewall of the channel. In certain embodiments, the microfluidic channel includes between 3 and 9 displacement elements, between 3 and 7 displacement elements or between 3 and 6 displacement elements, inclusive. In one instance, such as that depicted in FIG. 3A, the microfluidic channel includes 6 displacement elements.

Figures 5A, 5B:
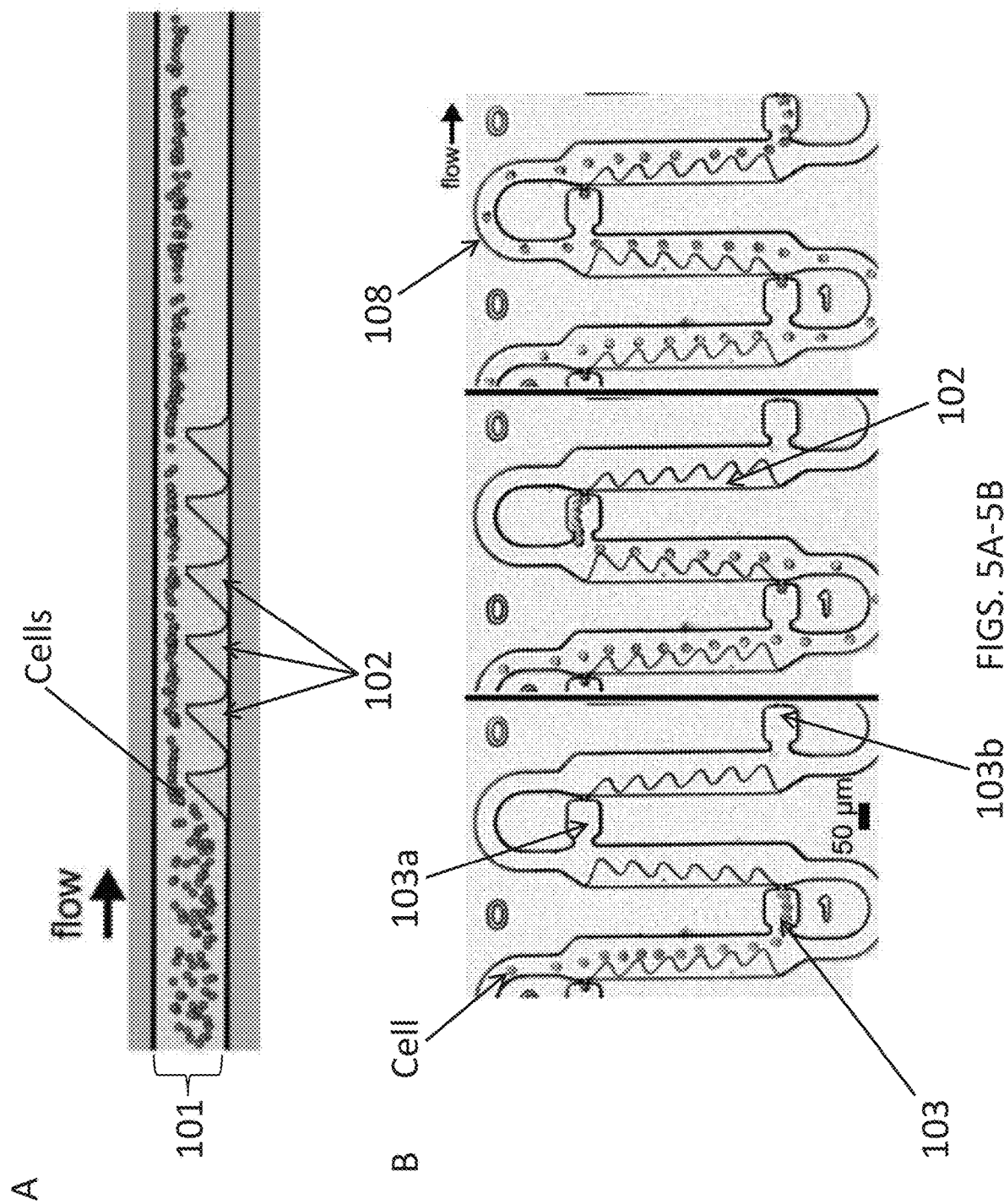
FIGS. 5A-5F: Time lapse of seeded flow of particles or cells through exemplary microfluidic devices of the present disclosure showing trapping of a single cell or particle of interest.

In some embodiments, the each of the at least one displacement element(s) (102) can be connected to form a single structure of interconnected displacement elements as shown, for example, in FIG. 5B. In other embodiments, each at least one displacement element can be a distinct and separate element that does not contact another displacement element as shown, for example, in FIGS. 1A-1B.

As shown in FIGS. 1A and 2A, the displacement elements each have a tapered geometry. As used herein the term "tapered" means having a first width (W1) at the base of the displacement element (i.e., the surface of the displacement element in contact with a surface of the microfluidic channel), and a second width (W2) that is smaller than the first width as height (H) increases. For example, a tapered displacement element has a fixed maximum height (measured in the direction extending toward into the microfluidic channel (101) toward the opposing sidewall) and a width that progressively decreases as the displacement element extends into the microfluidic channel. See FIG. 1A.

Figure 2B:
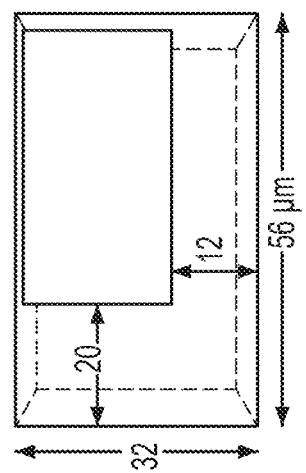
FIGS. 2A-2E: Description and function of exemplary displacement elements (102).
Figure 2A:
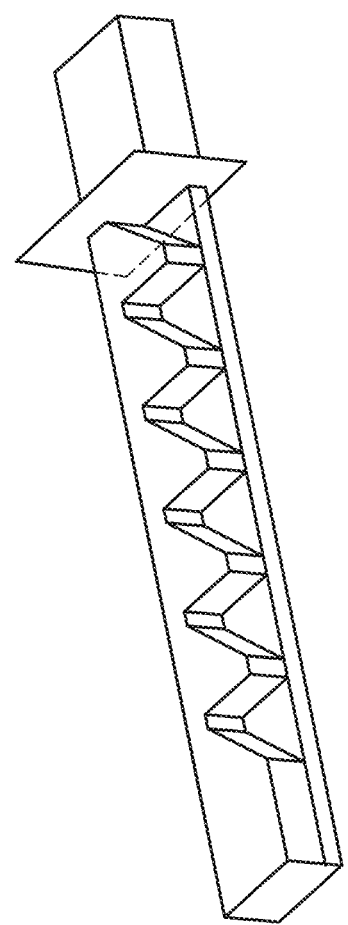
Figure 2C:
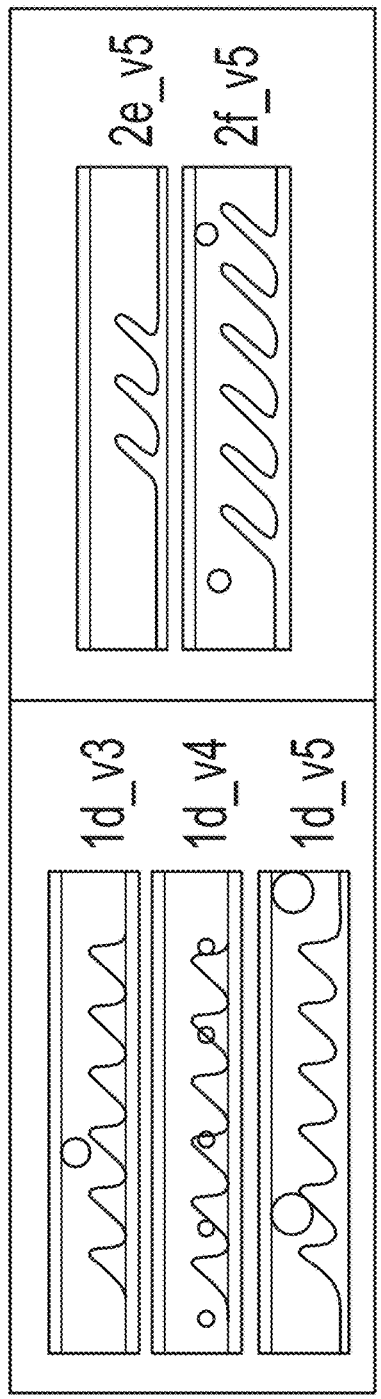

As shown in FIGS. 2B and 2C of the present disclosure, the height of each of the at least one displacement elements can be altered to modulate displacement of fluid flow and or materials therein (e.g., cells or particles). Furthermore, as shown in FIG. 2C the geometry and dimensions of the displacement elements alters displacement of cells or particles flowing through the microfluidic channel. As such, the dimensions of the displacement elements can be tailored to manipulate fluid flow and the flow path of cells or particles to be captured through the microfluidic channel.

Accordingly, in some embodiments, the maximum height of a displacement element is between 10 µm and 30 µm, between 10 µm and 25 µm, between 15 µm and 25 µm, between 17 µm and 23 µm, or between 18 µm and 22 µm. In a specific embodiment, the maximum height of a displacement element is between 10 µm and 25 µm, inclusive. In other embodiments, the maximum height of a displacement element is 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, or 30 µm. As shown in FIGS. 2A-2B, in certain embodiments, the maximum height of a displacement element is 20 µM.

In other embodiments, the displacement elements have a maximum height extending into the channel as defined by the distance between the topmost surface of the displacement element and the opposing wall of the microfluidic channel. Here, the distance between the topmost surface of the displacement element and the opposing wall of the microfluidic channel is about the size of a cell, such that the cell or particle can be arranged into a single-file as fluid containing a plurality of cells or particles flows down a microfluidic channel. As such, in certain embodiments, the distance between the topmost surface of the displacement element and the opposing wall of the microfluidic channel is between 10 µm and 45 µm or between 10 µm and 30 µm. In other embodiments, the distance between the topmost surface of the displacement element and the opposing wall of the microfluidic channel is between 10 µm and 40 µm, 14 µm and 40 µm, between 14 µm and 30 µm, between 14 µm and 25 µm, between 14 µm and 20 µm, 10 µm and 27 µm, between 10 µm and 26 µm, between 10 µm and 25 µm, between 15 µm and 25 µm, between 17 µm and 23 µm, or between 18 µm and 22 µm. In a specific embodiment, the distance between the topmost surface of the displacement element and the opposing wall of the microfluidic channel is between 10 µm and 26 µm, inclusive. In other embodiments, the distance between the topmost surface of the displacement element and the opposing wall of the microfluidic channel is 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm or, 45 µm.

In some embodiments, each of the at least one the displacement elements have uniform dimensions. In other embodiments, each displacement element in a plurality of displacement elements extend the same distance into the microfluidic channel towards the opposite sidewall of the microfluidic channel. In other instances and as shown in FIG. 1E, each of the displacement elements in a plurality of displacement elements, from start to finish, extends a distance greater toward the opposite sidewall of the microfluidic channel than the preceding displacement element in the plurality of displacement elements. In other embodiments, at least one of the displacement elements in a plurality of displacement elements have different dimensions than the other displacement elements. For example, at least two, at least three, at least four, at least five, at least six, at least seven, at least 8, or at least 9 of the displacement elements in a plurality of displacement elements can have different dimensions. In other embodiments, only 1, only 2, only 3, only 4, only 5, only 6, only 7, only 8 or only 9 of the displacement elements in a plurality of displacement elements differ from the dimensions of all the other displacement elements in the plurality of displacement elements.

In certain embodiments, such as those depicted in FIGS. 1C-1E and FIG. 3C the at least one displacement element is located in the microfluidic channel between two ports (105/105a) in a sidewall of the microfluidic channel. Here, the microfluidic device includes a first port by which a solution can be injected into the microfluidic channel (i.e., an input port) and another port from which solution and/or an encapsulated cell exits the microfluidic channel (i.e., an output port). In some embodiments, each of the at least one displacement elements are located in the microfluidic channel between an input port and a trapping chamber. In other embodiments, at least one displacement element is located upstream of the trapping chamber. In yet another embodiment at least one displacement element overlaps with at least a portion of the trapping chamber. In some embodiments, the input port is located upstream of the at least one displacement element. In one embodiment, the retrieval port is located downstream of the at least one displacement element. In other embodiments, the retrieval port is located downstream of the at least one trapping chamber.

The ports can have any dimensions or shape that permits the passage of a solution containing at least one cell or particle of interest into the microfluidic channel. For example, the port can be a circular opening in a sidewall of the microfluidic channel, a rectangular opening, a square opening or an amorphous shaped opening in the sidewall of the microfluidic channel. In specific embodiments, the port may be an opening in the sidewall of the microfluidic channel have a cross-sectional width and/or height of between 10 µm and 60 µm, 10 µm and 50 µm, between 10 µm and 40 µm, between 10 µm and 30 µm, between 10 µm and 20 µm, 10 µm and 25 µm, between 10 µm and 20 µm, between 20 µm and 60 µm, between 20 µm and 50 µm, between 20 µm and 40 µm, or between 20 µm and 30 µm.

As shown in FIGS. 1A-1F and 3A-3D, the microfluidic device of the present disclosure includes at least one trapping chamber (103) located downstream of the at least one displacement elements (102). Here, the trapping chamber(s) are configured to trap a single cell or particle present in a sample (e.g., solution) after the cell has passed at least a portion of the at least one displacement elements. A trapping chamber (103) has a first opening (104) that permits the flow of fluid and/or material from the microfluidic channel (101) into trapping chamber (103).

Figure 3A:
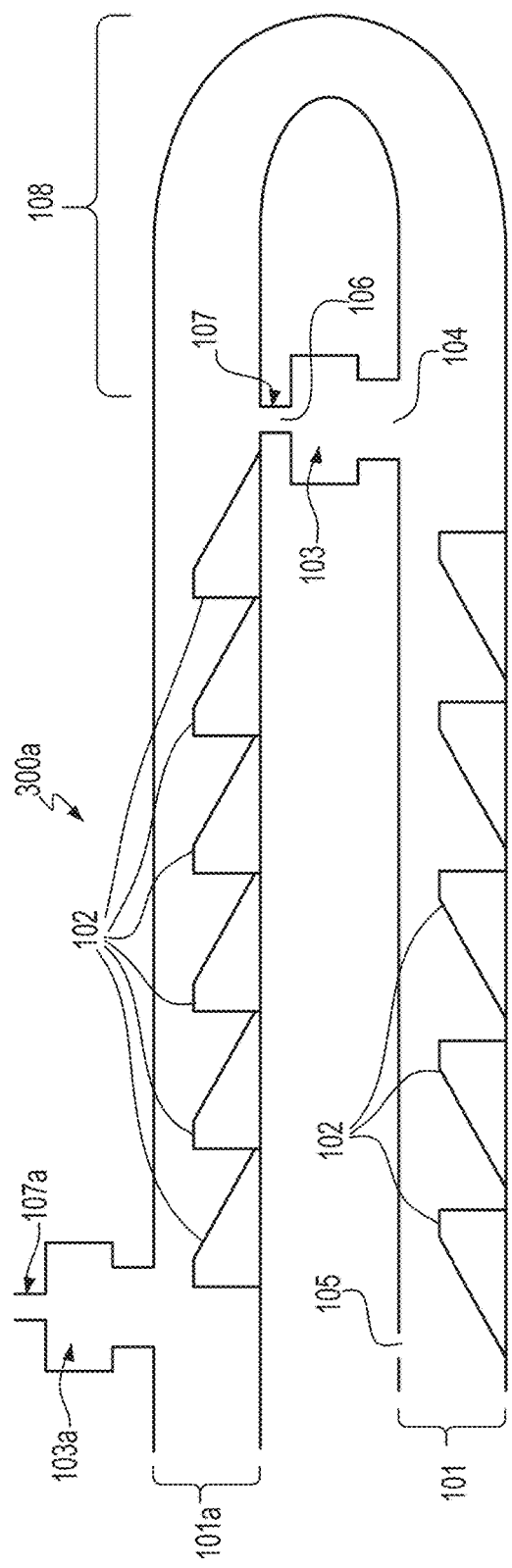

In some embodiments, each of the at least one displacement elements are located upstream of the first opening of said trapping chamber as shown in FIG. 1A. In other embodiments, at least one of the displacement elements is located upstream of the first opening of said trapping chamber and another of the at least one displacement elements is located downstream of the first opening of the trapping chamber. In yet another embodiment, at least one displacement element partially overlaps with a portion of the first opening of said trapping chamber, as shown in FIG. 3A In some embodiments, such as those shown in FIGS. 1D and 3C, the trapping chamber (103) at least two sidewalls extending in a direction away from the microfluidic channel (101) and the first opening (104) and another sidewall connecting the at least two sidewalls extending away from the first opening (104) to form an enclosed chamber. As depicted in FIG. 1D, in some instances the sidewalls extending away from the first opening (103) are parallel to each other. In other embodiments, the sidewalls extending away from the first opening and microfluidic channel are not parallel. For example, the trapping chamber can be a U-shaped enclosure, have one or more tapered sides or have an amorphous shape as set forth in FIG. 1A.

In one embodiment, such as that depicted in FIG. 1F, each of the at least one trapping chambers (103) have the same dimensions. In another embodiment, one or more of the at least one trapping chambers have different dimensions. In yet another embodiment, each of the at least one trapping chambers have different dimensions.

In some embodiments, such as those shown in FIGS. 1A-1C and 1E-1F, a trapping chamber has a second opening (106) at the opposite end of the chamber from the first opening (104) through which fluid can flow. Here, fluid will flow into the trapping chamber (103) from the microfluidic channel (101) through the first opening (104), traverse the trapping chamber and flow through the second opening (106) into a channel (107), i.e., a trapping channel. As such, in some embodiments, the second opening (106) in the trapping chamber is connected to another channel, such as a trapping channel (107).

In some instances, the second opening (106) is smaller than the first opening (103). In some embodiments, the first opening (103) has a width and height that permits the passage of fluid that includes at least one cell or particle of interest, and the second opening (106) has a width and height that permits the passage of fluid but not a cell or particle of interest. In a specific embodiment, the second opening (106) has a width that is narrower than the diameter of a cell or particle of interest. In another embodiment, the second opening has a width that is narrower than the diameter of a cell or particle of interest, but a height that is greater than the total height of the cell or particle, so as to prevent passage of the cell or particle through the second opening but permit the flow of fluid through the second opening. For example, the second opening may have a cross-sectional width and/or height between 10 μm and 40 μm, 14 μm and 40 μm, between 14 μm and 30 μm, between 14 μm and 25 μm, between 14 μm and 20 μm, 10 μm and 27 μm, between 10 μm and 26 μm, between 10 μm and 25 μm, between 15 μm and 25 μm, between 17 μm and 23 μm, between 18 μm and 22 μm or a combination thereof. In another embodiment, the second opening may have a cross-sectional width and/or height between 10 μm and 26 μm, inclusive. In other embodiments, the second opening may have a cross-sectional width and/or height can be 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 μm, 39 μm, 40 μm, 41 μm, 42 μm, 43 μm, 44 μm, 45 μm or a combination thereof.

Figure 4:
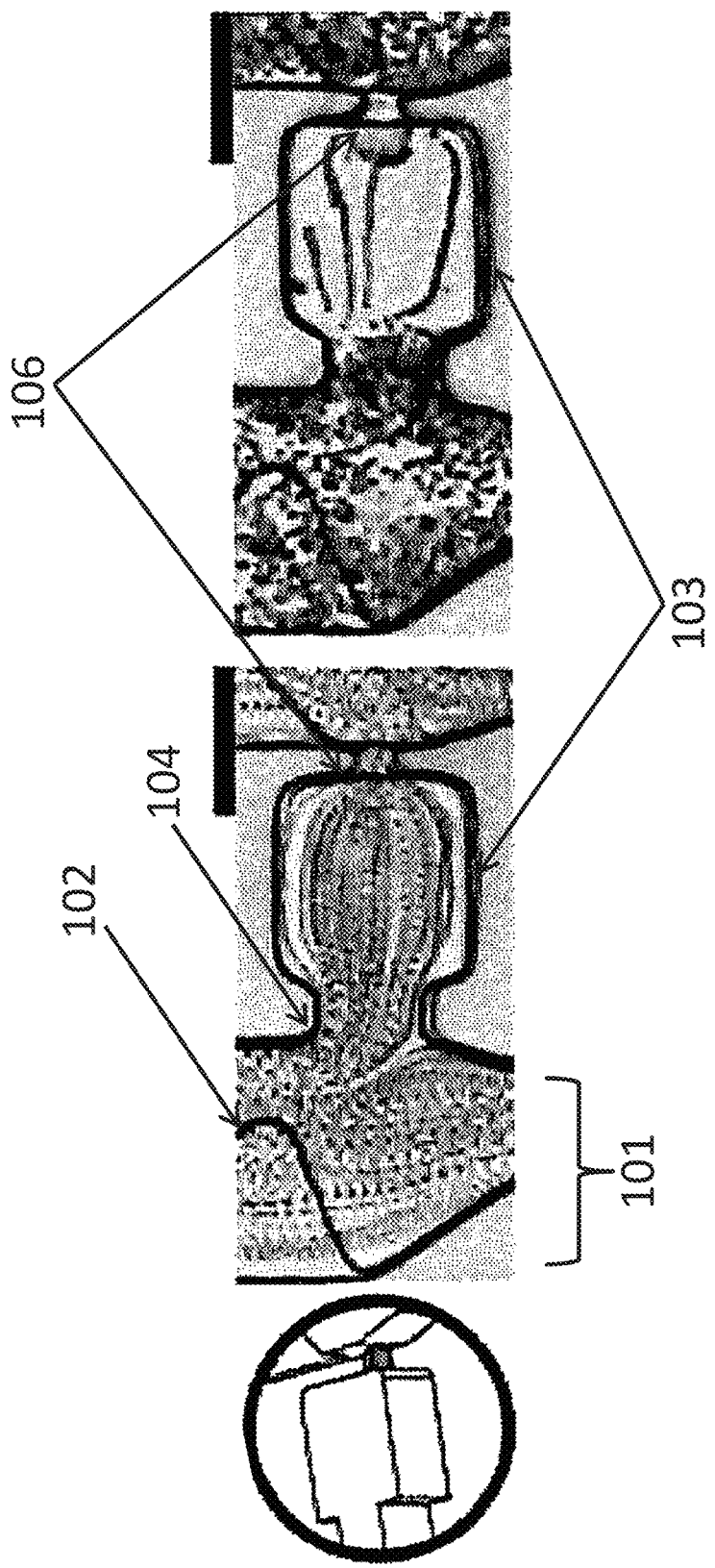
FIG. 4: Time lapse of seeded flow of particles or cells from a microfluidic channel (101) through a first opening (104) into vacant trapping chamber (103) and through a second opening (106) in the trapping chamber (left) and through a first opening (104) into "plugged" trapping chamber (103) (right). The right panel, shows the effects of the "plugging effect" on fluid flow through the trapping chamber (103) and trapping channel (107). Scale bars: 50 µm.

In certain embodiments, the second opening has dimensions that do not permit the passage of a cell, particle or any fluid. Here, once a cell or particle enters a trapping chamber it will "plug" in the second opening preventing the flow of fluid and material through the second opening or a trapping channel. When a cell or particle "plugs" the second opening of a trapping chamber fluid flow is diverted out of the trapping chamber ("plugging effect"), as shown in FIG. 4.

In some embodiments, such as those depicted in FIGS. 1C-1D, the microfluidic device of the present disclosure includes a capture element (109), whereby the capture element (109) protrudes into the first opening (104) of a trapping chamber (103). In certain embodiments, the capture element can be hook-shaped. See, e.g., FIGS. 3B and 3C. For example and as depicted in FIG. 1C, the capture element (109) can be a hook that protrudes into the first opening of the trapping chamber (103) and into a portion of the channel (101). In some embodiments and as shown in FIGS. 1D and 3C, the capture element (109) can be positioned downstream of the trapping chamber (103). In other embodiments, such as that depicted in FIGS. 1C and 3B, the capture element (109) can be positioned upstream of the trapping chamber (103).

In certain instances, the microfluidic device (100e) of the present disclosure includes a blocking rail (111) that traverses an inner portion of the trapping chamber (103). Here, the blocking rail (111) is affixed to the inner sidewalls of a trapping chamber (103) and positioned such that the blocking rail (111) will trap a passing cell or particle of interest, but will permit the flow of fluid over and/or under the blocking rail through the trapping chamber. See FIGS. 1E and 3D. In other embodiments, the blocking rail (111) can be configured to form a "pocket" in which a cell may be trapped. Here, the pocket can have a cross-sectional width of a about a cell, such as for example, between is between 10 μm and 40 μm, 14 μm and 40 μm, between 14 μm and 30 μm, between 14 μm and 25 μm, between 14 μm and 20 μm, 10 μm and 27 μm, between 10 μm and 26 μm, between 10 μm and 25 μm, between 15 μm and 25 μm, between 17 μm and 23 μm, or between 18 μm and 22 μm.

In another embodiment and as shown in FIGS. 1D and 3C, the microfluidic device (100d, 300c) of the present disclosure includes a pressurized control channel (110). Here, the pressurized control channel (111) overlies the outermost surface of a trapping chamber (103). In some instances, the pressurized control channel (111) is maintained at atmospheric pressure. In other instances, a positive pressure is applied to the pressurized control channel (111) such that the underlying trapping chamber (103) is compressed such that the contents of the trapping chamber are expelled from the chamber (103) through the opening (104) into the microfluidic channel (101). Here, the pressurized control channel can be maintained at 0.1 atmospheres (atm) to 1.0 atm, 0.2 atm to 1.0 atm, 0.3 atm to 1.0 atm, 0.4 atm to 1.0 atm, 0.5 atm to 1.0 atm, 0.6 atm to 1.0 atm, 0.7 atm to 1.0 atm, 0.8 atm to 1.0 atm, or 0.9 atm to 1.0 atm. In other examples, the pressurized control channel can be maintained at between 1 and 15 psi, 3 and 15 psi, 5 and 15 psi, 7 and 15 psi, 9 and 15 psi, 11 and 15 psi, 12 and 15 psi, 13 and 15 psi, 14 and 15 psi, or 15 psi. In other instances, such as when a positive pressure is applied to the pressurized control channel such that the underlying trapping chamber is compressed the pressure in the trapping chamber is greater than 1.0 atm, greater than 2.0 atm, greater than 3.0 atm, greater than 4 atm or higher. In some embodiments, the pressurized control channel can be pressurized to a pressure at between 15 and 30 psi, 17 and 30 psi, 19 and 30 psi, 21 and 30 psi, 23 and 30 psi, 25 and 30 psi, 26 and 30 psi, 27 and 30 psi, 28 and 30 psi, 30 to 40 psi, or greater. However, any pressure can be applied that is sufficient to compress the underlying trapping chamber, which can readily be determined by one of ordinary skill in the art.

As shown in FIGS. 3A-3E, in some instances, the microfluidic device of the present disclosure includes at least two microfluidic channels (101/101a) that are connected by a bypass channel (108). Here, the bypass channel (108) is located downstream of the at least one trapping chamber (103) of the first microfluidic channel (101) such that the bypass channel (108) connects two adjacent microfluidic channels (101/101a) forming a pathway through which fluid can flow. This enables sequential trapping and encapsulation of single cells using the microfluidic devices of the present disclosure.

In certain embodiments, the microfluidic device of the present disclosure includes 2, 3, 4, 5, 6 or more microfluidic channels arranged in fluid communication with one another, such that a bypass channel connects two adjacent microfluidic channels to form a microfluidic circuit. The microfluidic device can include any of the above-referenced microfluidic channels affixed to a trapping chamber. In some embodiments, the microfluidic device has at least 2 microfluidic channels that are the same, wherein each microfluidic channel is affixed to an identical trapping chamber. In other embodiments, all of the microfluidic channels and trapping chambers of the microfluidic device are the same.

In some embodiments, the exemplary microfluidic devices of the present disclosure include one or more ports in a sidewall of a microfluidic channel. Here, the microfluidic device includes a first port by which a solution (cells, particles, buffer, oil) can be injected into the microfluidic channel (i.e., an input port) and, optionally, another port from which solution and/or an encapsulated cell or particle exits the microfluidic channel (i.e., an output port). In some instances, the same port can be used as an input port and an output port.

In certain embodiments, the bypass channel is curved, such as for example, U-shaped. In one embodiment, the bypass channel (108) has the same cross-sectional diameter as the microfluidic channel. In other embodiments, the bypass channel is narrower, or wider than the microfluidic channel. In some embodiments, the overall length of the bypass channel (108) will affect the ability of the exemplary microfluidic devices to encapsulate cells by altering the rate at which an interface between immiscible solution and a cell- or particle-containing fluid travel through the microfluidic device. More specifically, the overall length of the bypass channel will be between 130 µm and 5000 µm, 200 µm and 4500 µm, 300 µm and 4000 µm, 300 µm and 3000 µm, 300 µm and 2000 µm, 300 µm and 1500 µm, 300 µm and 1400 µm, 300 µm and 1300 µm, 300 µm and 1200 µm, 300 µm and 1100 µm, or 300 µm and 1000 µm, inclusive. In a specific embodiment, the overall length of the bypass channel will be between 300 µm and 1000 µm, 350 µm and 1000 µm, 400 µm and 1000 µm, 500 µm and 1000 µm, 600 µm and 1000 µm, 700 µm and 1000 µm, 800 µm and 1000 µm. In a preferred embodiment, the overall length of the bypass channel will be between 300 µm and 1000 µm, which provides unique flow rates and paths that surprisingly enable several of the encapsulation methods of the present disclosure.

In some embodiments, the microfluidic device (300a, 300b, 300e) includes at least two microfluidic channels in fluid communication with one another through a bypass channel and at least one trapping channel affixed to a trapping chamber, whereby the trapping channel connects the trapping chamber(s) of a first microfluidic channel to an adjacent microfluidic channel. See FIG. 4. In specific embodiments, each of the microfluidic channels have at least one trapping chamber affixed to a trapping channel, whereby the trapping channel connects the trapping chamber(s) of a first microfluidic channel to an adjacent microfluidic channel. See, for example, FIGS. 3A-3B and 3E. In some embodiments, the microfluidic device has one or more capture elements located downstream or upstream of a trapping chamber. In certain embodiments, the microfluidic device (300b) has one or more capture elements located upstream of each trapping chamber. See FIG. 3B.

In yet other embodiments, the microfluidic device (300c) includes at least two microfluidic channels in fluid communication with one another through a bypass channel only. Here, at least one of the microfluidic channels have one or more enclosed trapping chambers as shown, for example, in FIG. 3C. As stated above, the dimensions of each enclosed trapping chamber may vary, so long as each trapping chamber is surrounded by a pressurized control channel, as shown in FIG. 3C. As depicted in FIG. 1D, in some instances the sidewalls extending away from the first opening are parallel to each other. In a specific embodiment, the sidewalls extending away from the first opening and microfluidic channel are not parallel. See FIG. 1A. In certain embodiments, the microfluidic device also includes a capture element positioned downstream of the first opening of a trapping chamber, as described above. In other embodiments, the microfluidic device has one or more capture elements located downstream of each trapping chamber. See FIG. 3C.

In some instances, as depicted in FIG. 3D, the microfluidic device of the present disclosure (300d) includes at least two microfluidic channels in fluid communication with one another through a bypass channel and at least one trapping channel, whereby the trapping channel connects the trapping chamber(s) of a first microfluidic channel to an adjacent microfluidic channel. See FIG. 4. In specific embodiments, each of the microfluidic channels have at least one trapping chamber affixed to a trapping channel, whereby the trapping channel connects the trapping chamber(s) of a first microfluidic channel to an adjacent microfluidic channel. Here, one of more of the trapping chambers can include a blocking rail as shown, for example, in FIG. 3D. As stated above, the blocking rail and trapping chamber can be configured in any manner known to one of ordinary skill in the art that permits the flow of fluid, but not cells or particles of interest, around, under or over the blocking rail through the trapping chamber and into the trapping channel.

Methods.

The inventors have identified several methods for trapping and encapsulating single cells or particles of interest for further isolation and analysis using the microfluidic devices of the present disclosure. Generally, efficient trapping of a single cell or particle in an aqueous solution containing a plurality of cells or an aqueous solution containing a homogeneous population of a particular particle of interest is performed by introducing a cell or particle to a microfluidic channel through a port located on a sidewall of a microfluidic channel. A positive pressure is applied to the microfluidic channel forcing the fluid contained therein to flow down the microfluidic channel over one or more displacement elements, which displace the flow and cells or particles, directing the cells or particles towards a capture chamber affixed to the microfluidic channel. A cell or particle is then trapped (captured) within the trapping chamber (such as, for example by plugging in a trapping channel or being restrained by a capture element or binding rail. Without being bound by any one particular theory, the location and geometry of the microfluidic channel, displacement elements, trapping chamber, trapping channel, capture element and/or binding rail increases resistance in the device and thus increases the flow toward the trapping chambers. This enables the devices of the present disclosure to include a shorter bypass channel, as set forth above, to connect adjacent microfluidic channels.

Next, encapsulation occurs when an immiscible fluid is introduced to the microfluidic channel through a port creating an interface with the aqueous solution. Using the methods disclosed herein, the interface can be manipulated to create aqueous droplets that encapsulate a single cell or particle trapped in a trapping chamber of a microfluidic device. More specifically, when an interface progresses inside a channel its direction can be controlled by: capillary effect, which is governed by the dimensions of the channel and flow-rate of fluid through a channel or series of channels; hydrodynamic resistance as governed by flow rate and viscosity of the liquid flowing through the channel; and wetting, which is controlled by the friction created by elements of the device.

Therefore, the present disclosure also provides methods for encapsulating single cells or particles from a sample using the microfluidic device(s) described above.

In one aspect of the present disclosure, a method for encapsulating single cells or particles of interest includes providing a first solution having at least one cell into a microfluidic channel of the device at a position upstream of at least one displacement element. In some instances, first solution is a homogeneous mixture of particles. Here, a positive pressure is applied to the microfluidic channel maintaining a desired rate of flow for the solution through the microfluidic device forcing the at least one cell or particle of interest through the microfluidic channel past the at least one displacement element, which directs the flow of the at least one cell or particle to the first opening in the trapping chamber. The cell or particle may be trapped by the first trapping chamber or, in embodiments where the device comprises more than one trapping chamber, the cell or particle may be trapped by a subsequent trapping chamber in the microfluidic device. The cell or particle remains in the trapping chamber while the first solution continues to flow downstream through the microfluidic device.

As used herein the terms "fluid" and "solution" are used interchangeably to refers to a substance that tends to flow and to conform to the outline of its container, such as a channel. Typically, fluids are materials that are unable to withstand a static shear stress. When a shear stress is applied to a fluid, it experiences a continuing and permanent distortion. Typical fluids include liquids (e.g., water or aqueous solutions), supercritical fluids, and the like. The fluid may have any suitable viscosity, for example, a viscosity similar to water (e.g., as in an aqueous solution) or oil. In specific instances, multiple fluids can be provided to a microfluidic device. The fluids can be miscible or immiscible. Those of ordinary skill in the art can select suitable miscible or immiscible fluids, using contact angle measurements, tables of interfacial energies, and the like. The skilled artisan can also modulate interfacial tension between two fluids to obtain desired properties of the fluids such as jetting of one fluid in the other, onset of Rayleigh-Plateau instability, shear-driven drift, and the like, using suitable surfactants.

The first solution can be an aqueous liquid that includes one or more cells such as, for example, a plurality of cells. In certain instances, the first solution can be an aqueous solution that includes a plurality of particles that has been processed to contain only one type of particle, such as a nucleus, organelle or bead (i.e., a "homogenous mixture of particles") In some embodiments, the first solution can include a buffer reagent and/or dissolved ions. In one embodiment, the solution can be an aqueous buffer including, for example, a pluronic F-68 solution and phosphate buffered saline. In other embodiments the first solution includes a surfactant. In other embodiments, solution could contain antibodies, cell lysis solution, reagents such as enzymes (e.g., transposases, polymerases) or other materials known to those of ordinary skill in the art used to perform amplification (PCR) or nucleotide sequence tagging and/or barcoding.

A "sample" refers to a fluid capable of flowing through a channel. Thus, a sample can include a fluid suspension of biologically-derived particles (such as cells, organelles, nuclei, etc.). The sample can comprise a material in the form of a fluid suspension that can be driven through microfluidic channels can be used in the systems and methods described herein. For example, a sample can be obtained from an animal, water source, food, soil, or air. If a solid sample is obtained, such as a tissue sample or soil sample, the solid sample can be liquefied or solubilized prior to subsequent introduction into the system. A sample can generally include suspensions, liquids, and/or fluids having at least one type of particle, cell, and/or bead. Further, focusing can produce a flux of particles enriched in a first particle based on size. Cells can be, alive or fixed, such as adult red blood cells, fetal red blood cells, trophoblasts, fetal fibroblasts, white blood cells, epithelial cells, tumor cells, cancer cells, hematopoeitic stem cells, bacterial cells, mammalian cells, plant cells, neutrophils, T lymphocytes, B lymphocytes, monocytes, eosinophils, natural killer cells, basophils, dendritic cells, circulating endothelial cells, antigen specific T-cells, and fungal cells. Samples can be diluted or concentrated to attain a predetermined ratio before and/or during introduction of the sample into the system. In general, the cell to volume ratio can be less than about 50%. In other embodiments, cell to volume ratios can be less than about 40%, 30%, 20%, 10%, 8%, or 6%. More particularly, in some embodiments, cell to volume ratios can be in a range of about 0.001% to about 5%, e.g., in a range of about 0.01% to about 4%. In general, a maximum cell to volume ratio for a specified cell size and channel geometry can be determined by one of ordinary skill in the art. The term "particle" can also include a particle, such as non-biologically derived sphere (i.e., a bead) having predetermined dimensions. In some instances, the bead can be conjugated to another particle or cell.

As used herein, the term "flow" refers to the passage of a fluid in a specific direction, i.e., downstream, which may change over time. The flow may be continuous and/or discontinuous. The flow may be laminar or turbulent. In specific embodiments of the present disclosure the flow is laminar. A continuous flow may for example move a solution containing one or more cells or particles through a channel. As such, the flow path, shape or rate may depend on the shape of the channels in which the fluid travels or displacement elements therein.

Various techniques exist for moving a sample through a microfluidic channel. For example, a microfluidic system can include a pumping mechanism for introducing and moving the fluid sample into and through one or more microfluidic channels. The pumping mechanism can also regulate and control a flow rate within the channels as needed. A specific pumping mechanism can be provided in a positive pumping configuration, in a negative pumping configuration, or in some combination of both. In one embodiment, a sample can be introduced into the inlet and can be pulled into the system under negative pressure or vacuum using the negative pumping configuration. A negative pumping configuration can allow for processing of a complete volume of sample, without leaving any sample within the channels. Exemplary negative pumping mechanisms can include, but are not limited to, syringe pumps, peristaltic pumps, aspirators, and/or vacuum pumps. In other embodiments, a positive pumping configuration can also be employed. A sample can be introduced into the inlet and can be injected or pushed into the system under positive pressure. Exemplary positive pumping mechanisms can include, but are not limited to, syringe pumps, peristaltic pumps, pneumatic pumps, displacement pumps, and/or a column of fluid. Oscillations caused by some pumping mechanisms, such as a peristaltic pump, can optionally be damped to allow for proper focusing within the channels.

Flow rates within the channels can be regulated and controlled. For instance, any number and variety of microfluidic valves can also be included in the system to block or unblock the pressurized flow of particles through the channels. The microvalve can include one or more mobile diaphragms or flexible membranes formed in a layer above a channel branch, inlet, or outlet such that upon actuation, the membrane is expanded up to decrease resistance within a channel branch, inlet, or outlet, or expanded down into the channel to increase resistance within the same. Further details and discussion of such microfluidic diaphragms are disclosed in PCT Publication No. PCT/US2006/039441 entitled, "Devices and Methods for Cell Manipulation" filed Oct. 5, 2007 and incorporated herein by reference in its entirety. Optionally, one or more microfluidic, size-based separation modules or filters can be included to prevent clogging within the channels by preventing certain cell or particle sizes or cell types from entering the channels and/or to facilitate collection of cells or particles for downstream processing.

The fluid stream of cells or particles of interest can pass through a port (inlet or outlet) of a microfluidic channel through a nozzle and into a medium suitable to induce droplet formation from the fluid stream. Droplet formation of the fluid can be induced by injecting the fluid into a second immiscible liquid, as described by Utada et al, Phys. Rev. Lett. 99, 094502 (2007), incorporated herein by reference in its entirety. The mechanism of droplet formation of the fluid is related to the presence of the surrounding viscous liquid. A liquid forced through an orifice will ultimately break into droplets at slow flows, whereas at faster flows the liquid forms a thin stream that breaks into droplets away from the orifice; these are the dripping and jetting regimes.

In some embodiments, of the present disclosure, the trapping step includes providing a solution comprising at least one cell or particle of interest, preferably a plurality of cells or particles by injecting the cells or particles through an inlet port located upstream of at least one displacement element. In some embodiments, the solution can be injected at a flow rate of 0 to 40 µl/hr, 10 to 40 µl/hr, 15 to 40 µl/hr, 20 to 40 µl/hr or 30 to 40 µl/hr. In methods specific to the trapping and encapsulation of non-biological particles such as particle containing solution can be injected at a flow rate of up to 100-200 µl/hr, 100-150 µl/hr, 100 µl, or higher. In other embodiments, the cell- or particle-containing solution can be injected at a flow rate between 1 µl/hr and 20 µl/hr, 5 µl/hr and 20 µl/hr, 6 µl/hr and 20 µl/hr, 1 µl/hr and 15 µl/hr, 1 µl/hr and 10 µl/hr, 5 µl/hr and 10 µl/hr, 6 µl/hr and 10 µl/hr or 1 µl/hr and 8 µl/hr. In some embodiments, the cell or particle-containing solution can be injected at a flow rate of 1 µl/hr, 2 µl/hr, 3 µl/hr, 4 µl/hr, 5 µl/hr, 6 µl/hr, 7 µl/hr, 8 µl/hr, 9 µl/hr, 10 µl/hr, 11 µl/hr, 12 µl/hr, 13 µl/hr, 14 µl/hr, 15 µl/hr, 16 µl/hr, 17 µl/hr, 18 µl/hr, 19 µl/hr, 20 µl/hr or greater.

In a specific embodiment where the cells are living, the cell containing solution is injected at flow rate of between 6 µl/hr and 10 µl/hr. In one example, the cell containing solution is injected at flow rate of 8 µl/hr. In another embodiment, where the cells are fixed, the cell containing solution is injected at flow rate of between 18 µl/hr and 22 µl/hr. In a specific embodiment, the cell containing solution is injected at flow rate of 20 µl/hr.

As shown in FIGS. 5A-5B, the cells flow downstream through the microfluidic channel (101) over at least one displacement element (102), where the cells are displaced and focused toward a trapping chamber (103, 103a, 103b), where a single cell is captured in each subsequent trapping chamber.

In some embodiments, such as those depicted in FIGS. 4 and 5A-5B, the cells or particles are trapped in a trapping chamber (103) by flowing through the first opening (104) of the trapping chamber through the trapping chamber (103) and "plugging" the trapping channel (107) by at least partially blocking in the second opening (106). In some instances, the second opening (106) and trapping channel are designed so that a single cell or particle of interest will completely plug the trapping channel (107) by blocking all fluid flow through the trapping channel (i.e., bypass mode, wetting mode). In other embodiments, the second opening and trapping channel is designed so that a single cell or particle plugs in the second opening (106) or the trapping channel (107) and only partially blocks the flow of fluid through the trapping channel (i.e., sweeping mode).

Figures 5C, 5D, 5E:
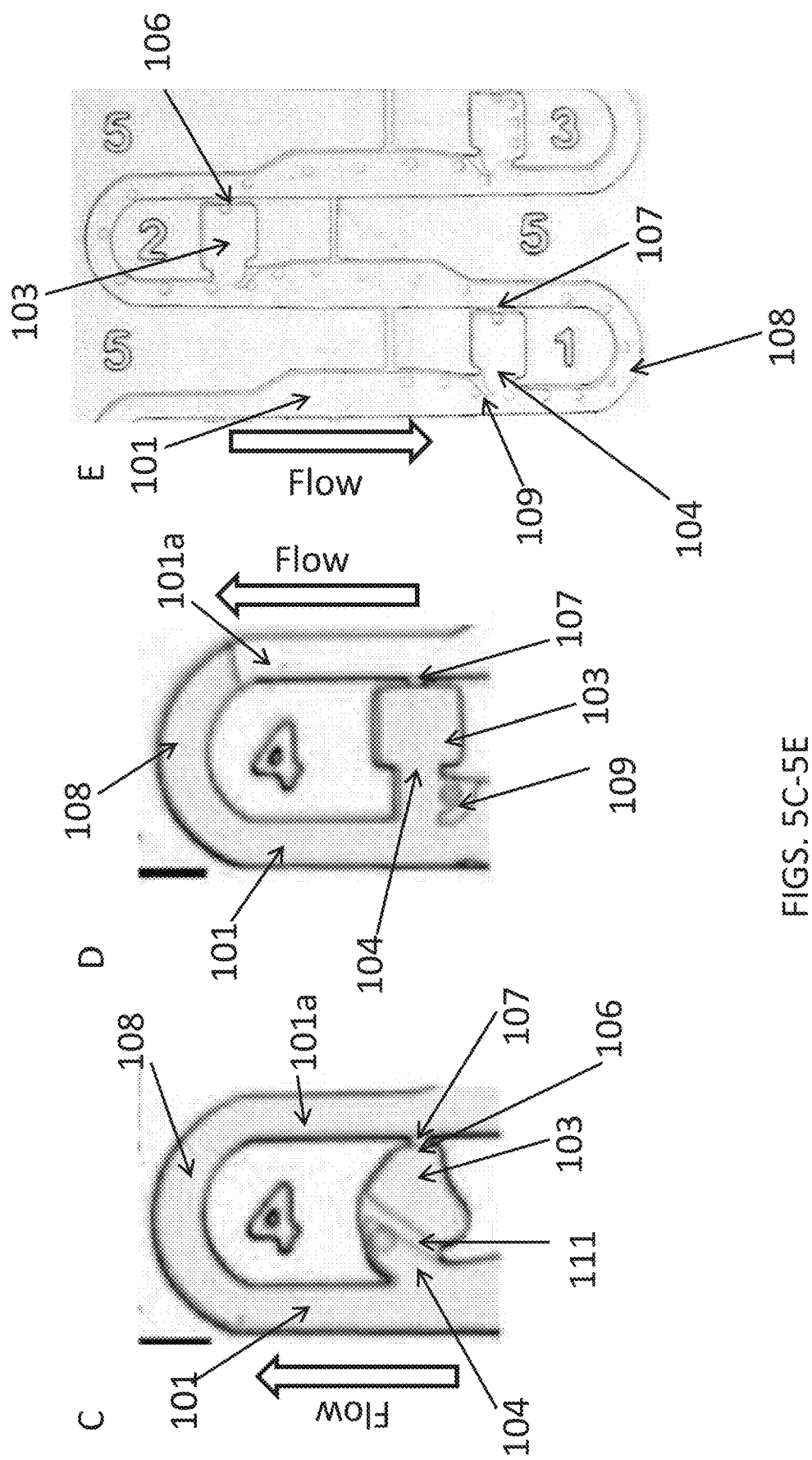

In other embodiments as depicted in FIG. 5C, a cell or particle provided to the microfluidic channel (101) in an aqueous buffer solution is captured in a trapping chamber (103) by flowing through the first opening (104) of a trapping chamber that includes a blocking rail (111). Here, the cell or particle flows downstream over displacement elements (not shown) and is directed into a trapping chamber (103) including a blocking rail (111). Once the cell or particle is contacted by the blocking rail (111), it is guided into a "pocket" where the cell remains trapped. As depicted in FIG. 5C the aqueous cell- or particle-containing solution can flow freely around the blocking rail (111) through the trapping chamber (103) into an adjacent microfluidic channel (101a).

In another embodiment as shown in FIG. 5D, a cell or particle is trapped in a trapping chamber (103) by flowing downstream over displacement elements (not shown) where it is directed toward a capture element (109) extending into a portion of the microfluidic channel (101) and the first opening (104) of the trapping chamber (103). The cell or particle then remains trapped by a hook shaped capture element (109) where it remains until encapsulation.

In one embodiment as shown in FIG. 5E, a cell or particle is trapped in a trapping chamber (103) containing a first opening (104) and a second opening (106) affixed to a trapping channel (107) by flowing the cell or particle downstream through the microfluidic channel (101) over displacement elements (102) where it is directed toward a capture element (109) extending into a portion of the microfluidic channel (101) and the first opening (104) of the trapping chamber (103). Here, the cell or particle flows into the trapping chamber (103) where a single cell is pulled toward the trapping channel (107) and plugged, as described above.

Figure 5F:
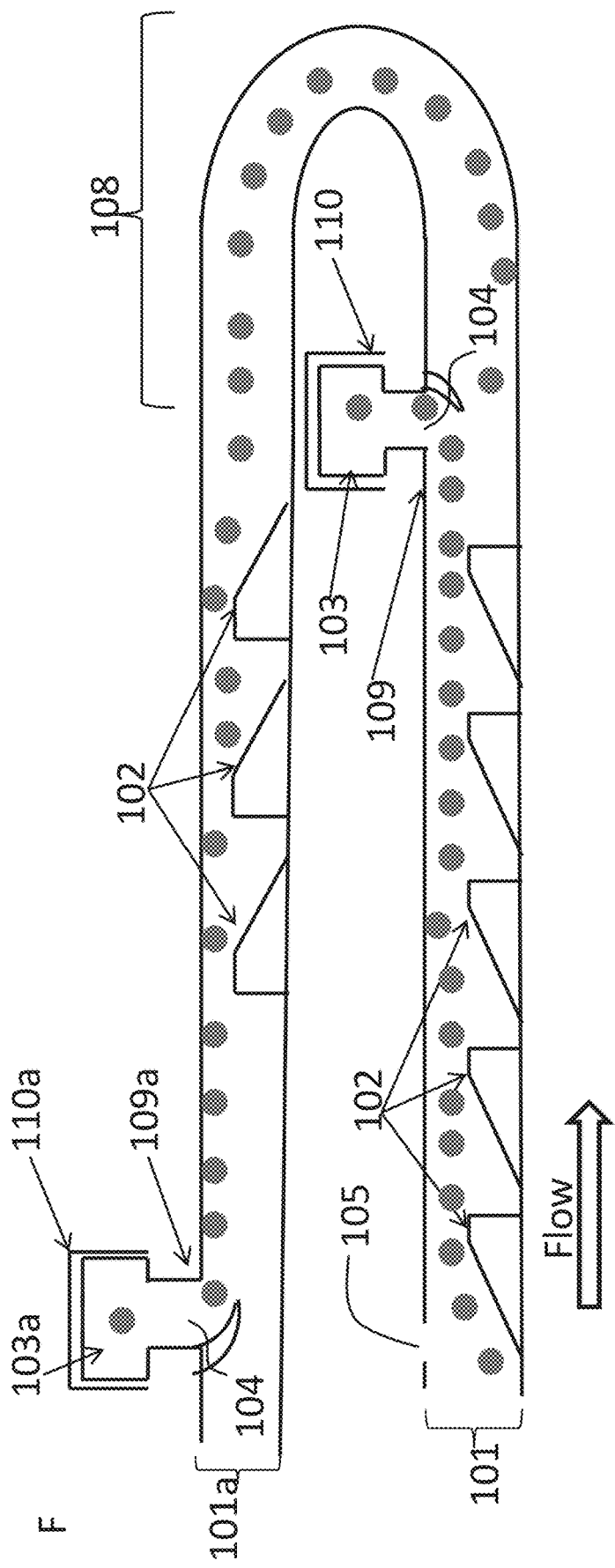

In yet another embodiment, which is depicted in FIG. 5F, a cell or particle is captured by flowing downstream over displacement elements (102) where it is directed toward a capture element (109) extending into a portion of the microfluidic channel (101) and the first opening (104) of a trapping chamber (103) which does not have a second opening and is not in fluid communication with a trapping channel. Here, the trapping chamber (103) has a pressurized control channel (110) on the outer surfaces of the trapping chamber. The cell or particle is then directed into the trapping chamber by fluid flow wherein a cell remains until encapsulation. In some embodiments, the cell or particle can remain trapped in the capture element adjacent to the trapping chamber.

Once a cell or particle is trapped by the trapping chamber and/or capture element the cell or particle can then be encapsulated in a droplet. Generally, during the encapsulation step, a second solution that is different than the first cell- or particle-containing solution is introduced to the microfluidic channel through a port (i.e., input port). A pressure is then applied to the microfluidic channel to direct the second solution to flow in a desired direction toward the trapping chamber(s) containing a trapped cell. Here, the second solution creates an interface with the first solution present in the microfluidic device. As the interface progresses through the microfluidic device, the bulk of the interface moves at a speed and direction is controlled by the flow rate and, in some instances by the dimensions of the channels, as set forth herein.

The port used to provide the second solution to the microfluidic channel can be the same as the port used to inject the first cell- or particle-containing solution, or it can be different.

In some embodiments, the second solution is an immiscible fluid, such as oil or an organic solvent. In certain embodiments, the liquid is an oil, such as those known to ordinary skill in the art. In specific embodiments, the solution is mineral oil, vegetal oil, silicone oil, or fluorocarbon oil (e.g., FC40 and HFE7500 fluoronated oil).

In some embodiments, a pressure is applied to the microfluidic device so that the second solution flows in the same direction as the first solution.

In embodiments where a cell or particle is trapped using any of the methods set forth in FIGS. 5B-5D and 5F, the second solution flows in the same direction as the first solution. Therefore, the interface between the first solution and the second solution moves through the device in the same general direction as the first solution.

Figure 6A:
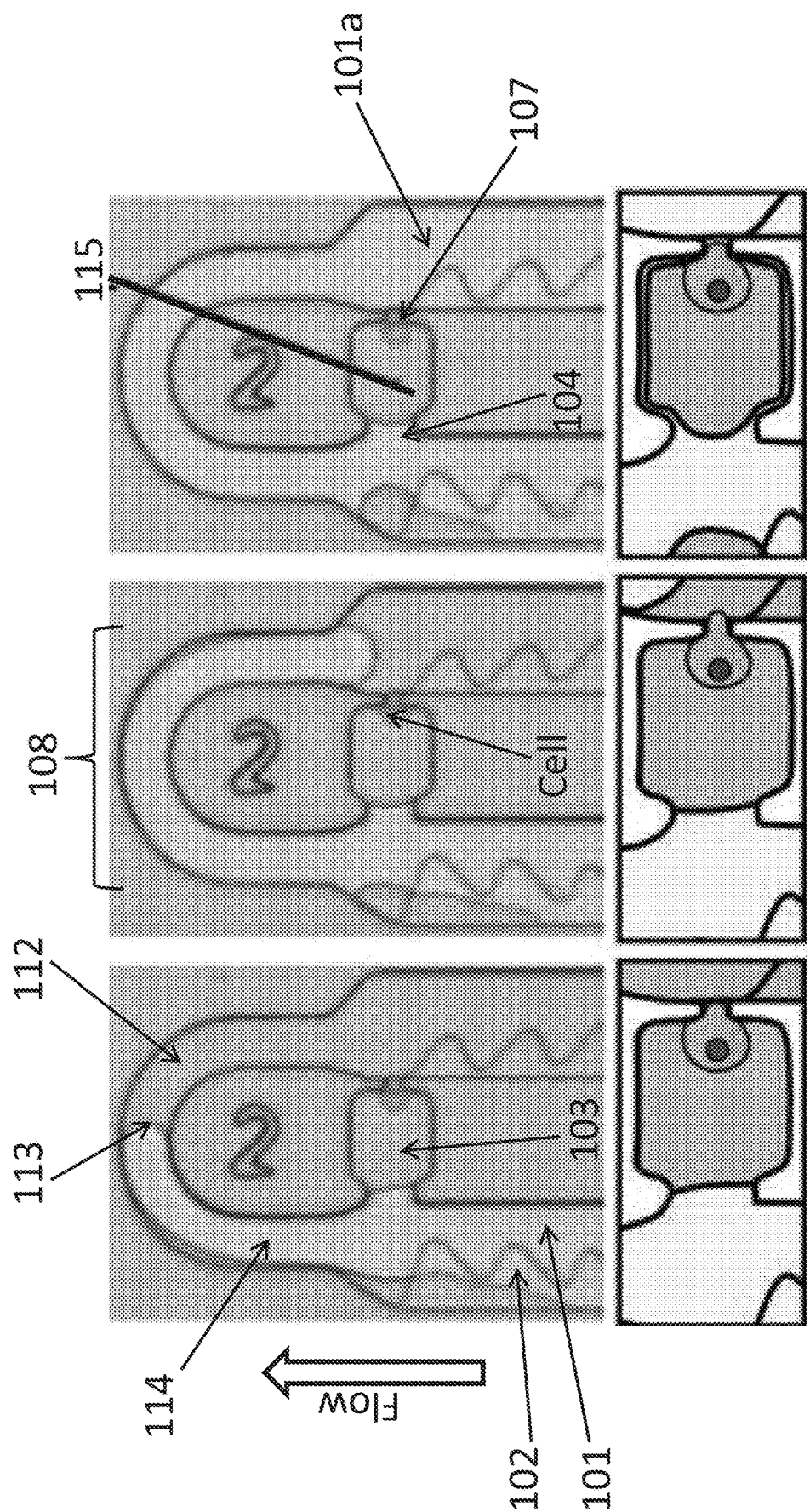
FIGS. 6A-6E: Depictions of exemplary single cell or particle of interest encapsulation methods of the present disclosure.

For example, in the exemplary encapsulation method shown in FIG. 6A, encapsulation of a cell or particle of interest in a droplet trapped using the trapping method depicted in FIG. 5B using the microfluidic devices of FIG. 3A occurs by injecting a second solution (114) that is immiscible with regard to the first solution (112) such that the two solutions form an interface (113) in the microfluidic channel (101). Here, the interface progresses through the microfluidic device in the same direction that the first solution (112) moved through the microfluidic device. As the second solution flows downstream toward the trapping chamber (103), a second interface between the first solution and the second solution is formed in the first opening (104) of the trapping chamber. In this exemplary encapsulation method, the second interface is formed in the first opening of the trapping chamber because the trapped cell or particle blocks the trapping channel preventing flow from being directed into the trapping chamber. Also, the flow rate, bypass channel and channel dimensions enable the formation of the first interface before a wetting film is formed on inner sidewalls of the microfluidic device. See FIG. 6A. In this embodiment, the flow rate of the second solution is sufficiently high enough to prevent wetting ahead of the interface and low enough not to damage the cell. For example, the flow rate is between 6 µl/hr and 10 µl/hr in instances when a live cell is captured. In a specific embodiment where live cells are trapped and encapsulated, the second solution cell is injected at a flow rate of 8 µl/hr. In embodiments where the cells in a sample are fixed, the second solution is injected at a flow rate of between 6 µl/hr and 22 µl/hr, 10 µl/hr and 20 µl/hr, 15 µl/hr and 20 µl/hr, or 18 µl/hr and 22 µl/hr. In a specific embodiment, the second solution is injected at a flow rate of 20 µl/hr. Next, the first interface (113) progresses through the bypass channel (108) into a second adjacent microfluidic channel (101a) that is connected to the trapping chamber (103) by a trapping channel (107). Since, the first interface must flow through the bypass channel and not be redirected into the trapping chamber, it is essential that the bypass chamber be configured for low resistance as set forth above. When the first interface (113) moves downstream of the trapping channel in the second adjacent microfluidic channel (101a) a droplet encapsulating the single cell or particle trapped in the trapping chamber is formed due to a change in pressure across the trapping channel that releases the plugged cell or particle from the trapping channel into an aqueous droplet having the same dimensions as the trapping chamber. See FIG. 6A.

In another exemplary encapsulation method of the present disclosure, encapsulation of a cell or particle in a droplet trapped using the trapping method depicted in FIG. 5B occurs by injecting a second solution (114) that is immiscible with regard to the first solution (112) such that the two solutions form an interface (113) in the microfluidic channel (101). Again, the interface progresses through the microfluidic device in the same direction that the first solution (112) moved through the microfluidic device. As the second solution flows downstream toward the trapping chamber (103), the flow rate of the second solution (114) maintained at a flow rate that causes a thin precursor film of second solution (oil) to form ("wetting") on the inner sidewalls of the microfluidic device ahead of the interface (113). This directs the first interface (113) to progresses toward the bypass channel and into the trapping chamber (103) through the trapping channel (107). Once the second solution wets the inner sidewalls of the trapping chamber (103) and flows into the trapping channel (107) the second solution surrounds the first solution containing the trapped cell or particle forming a droplet (115) prior to the first interface reaches the trapping channel in the second adjacent microfluidic channel (101a). See FIG. 6B. In this method, the flow rate is maintained at a rate of less than 6 µl/hr. In certain embodiments, the low flow rate for this encapsulation method is maintained at a rate of less than 1 µl/hr. In some non-limiting examples, the flow rate is between 0.1 µl/hr and 1.0 µl/hr, 0.2 µl/hr and 1 µl/hr, 0.3 µl/hr and 1 µl/hr, 0.4 µl/hr and 1 µl/hr, 0.5 µl/hr and 1 µl/hr, 0.6 µl/hr and 1 µl/hr, 0.7 µl/hr and 1 µl/hr, 0.8 µl/hr and 1 µl/hr or 0.9 µl/hr and 1 µl/hr, inclusive. In a specific embodiment, the flow rate is between 1 µl/hr and 6 µl/hr, 1 µl/hr and 5 µl/hr, 1 µl/hr and 4 µl/hr, 1 µl/hr and 3 µl/hr or 1 µl/hr and 2 µl/hr.

Figure 3B:
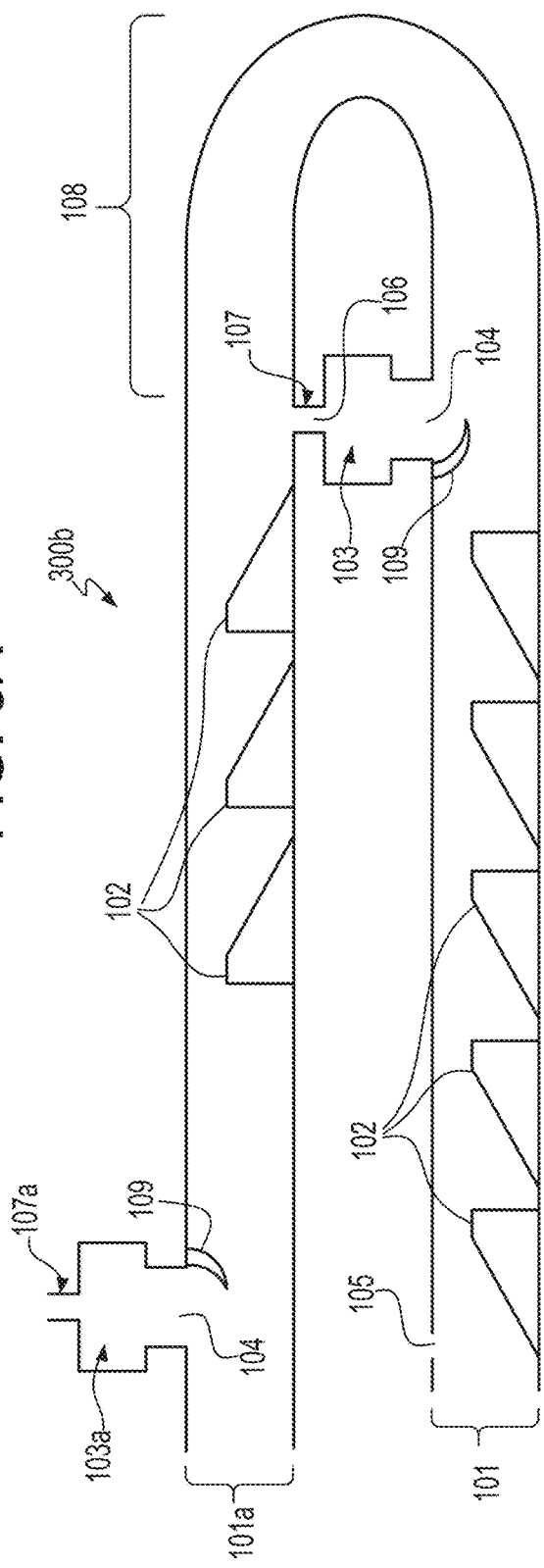
Figure 3E:
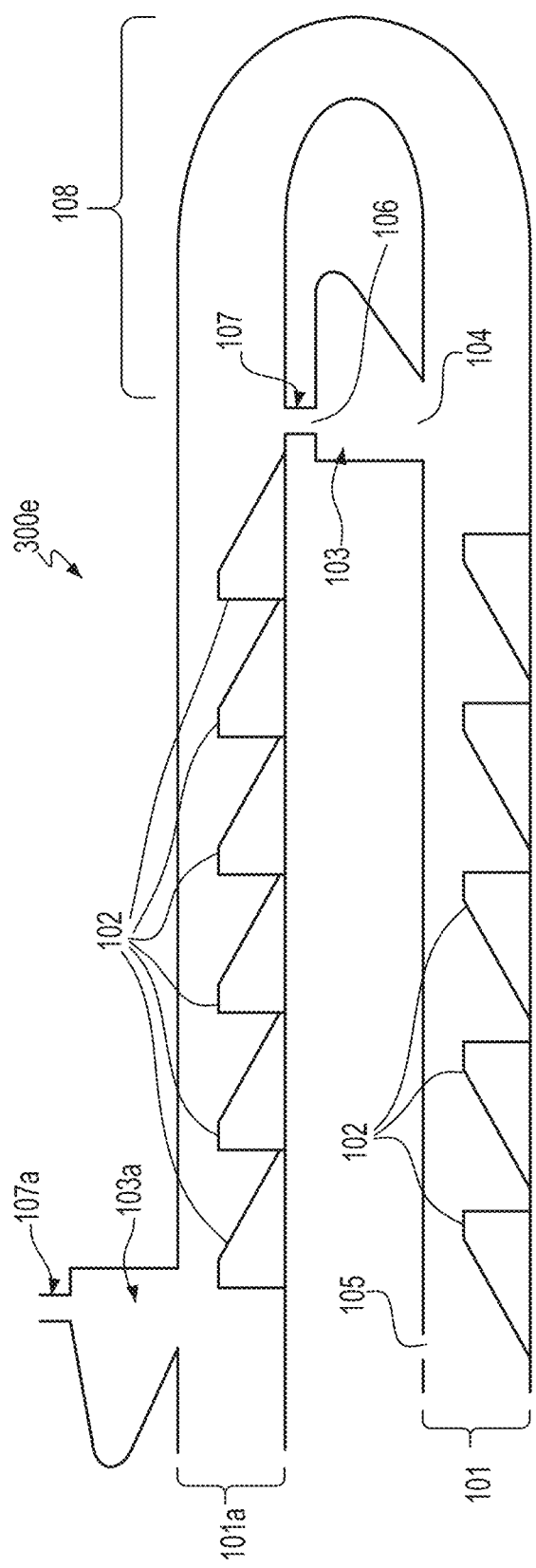

In a third exemplary encapsulation method, encapsulation of a cell or particle in a droplet trapped using the trapping method depicted in FIG. 5B and the device of FIG. 3E occurs by injecting a second solution (114) that is immiscible with regard to the first solution (112) such that the two solutions form an interface (113) in the trapping chamber (103). Again, the interface progresses through the microfluidic device in the same direction that the first solution (112) moved through the microfluidic device. However, in this trapping method the second opening (106) and/or the trapping channel (107) has a cross-sectional diameter that is not fully blocked by the cell or particle plugged therein. Hence, as the second solution flows downstream toward the trapping chamber (103), the second solution will flow into the trapping chamber (103) and through the trapping channel (107) releasing the cell or particle from the trapping channel (107) and "sweeping" the cell or particle into the trapping chamber (103) where it forms a droplet (115) encapsulating the trapped cell or particle of interest. See FIG. 6C. An additional feature of this encapsulation method is that additional trapping steps may be conducted in the same trapping chamber after a first encapsulation step is completed because the trapping channel (107) is unobstructed once the first cell or particle is encapsulated. Thus allowing injection of a train of droplets through a port, which flow downstream toward and into a trapping chamber containing a droplet, such that multiple droplets are maintained within the same trapping chamber. The second droplet could then be fused either chemically or using an electrical field delivered by on-chip electrodes to the first droplet.

In a fourth exemplary embodiment, encapsulation of a cell or particle in a droplet trapped using the trapping method depicted in FIG. 5C using the device shown in FIG. 3D occurs by injecting a second solution (114) that is immiscible with regard to the first solution (112) such that the two solutions form an interface (113) in the trapping chamber (103). Again, the interface progresses through the microfluidic device in the same direction that the first solution (112) moved through the microfluidic device. However, in this trapping method the second opening (106) and/or the trapping channel (107) is not blocked by the cell or particle of interest because the cell or particle is separated from the trapping channel and second opening by the blocking rail (111). Hence, as the second solution flows into the trapping chamber (103) around the blocking rail (111) and through the trapping channel (107) forming a droplet (115) within a "pocket" created by the blocking rail (111) that encapsulates the single, trapped cell particle. See FIG. 6D.

In a fifth exemplary embodiment, encapsulation of a cell or particle of interest in a droplet trapped using the trapping method depicted in FIG. 5D using the microfluidic devices of FIG. 3C occurs by injecting a second solution (114) that is immiscible with regard to the first solution (112) such that the two solutions form an interface (113) in the microfluidic channel (101). Here, the interface progresses through the microfluidic device in the same direction that the first solution (112) moved through the microfluidic device. As the second solution flows downstream toward the trapping chamber (103), a second interface between the first solution and the second solution is formed in the first opening (104) of the trapping chamber. In this encapsulation method, the second interface is formed in the first opening of the trapping chamber because the trapping chamber is enclosed except for the opening; hence, there is no flow through the trapping chamber. Also, the flow rate, bypass channel and channel dimensions enable the formation of the first interface before a wetting film is formed on inner sidewalls of the microfluidic device. See FIG. 6A. This results in a droplet being formed that encapsulates the single-trapped cells, whereby the droplet has the same dimensions as the trapping chamber.

In a sixth exemplary embodiment, the encapsulation of a single cell or particle trapped using the device of FIG. 1C or 3B occurs by injecting a second solution (114) that is immiscible with regard to the first solution (112) such that the two solutions form an interface (113) in the microfluidic channel (101). Here, the interface (113) progresses through the microfluidic device in the same direction that the first solution (112) moved through the microfluidic device. In this instance, flow of the second fluid into the trapping channel is restricted because the flow rate pushes the second solution past the trapping channel opening in a microfluidic channel to the bypass channel. As such, when a cell or particle is trapped using the microfluidic device of FIG. 1C or 3B and the method set forth in FIG. 5D will force the second solution to flow downstream past the trapping channel (107) toward the bypass channel (108). As the second solution flows past the trapping channel (107) the cell or particle will remain in the trapping chamber due to the location of the hook like capture element (109) that extending into at least a portion of the first opening (104) of the trapping chamber (103). Then, as the interface (113) progresses into the microfluidic channel toward the first opening (104) in the trapping chamber (103) an interface (113) at the first opening (104) in the trapping chamber (103) is formed, causing a droplet (115) encapsulating the trapped cell or particle to form having the same dimensions of the trapping chamber (103). See FIG. 6E.

Figure 6B:
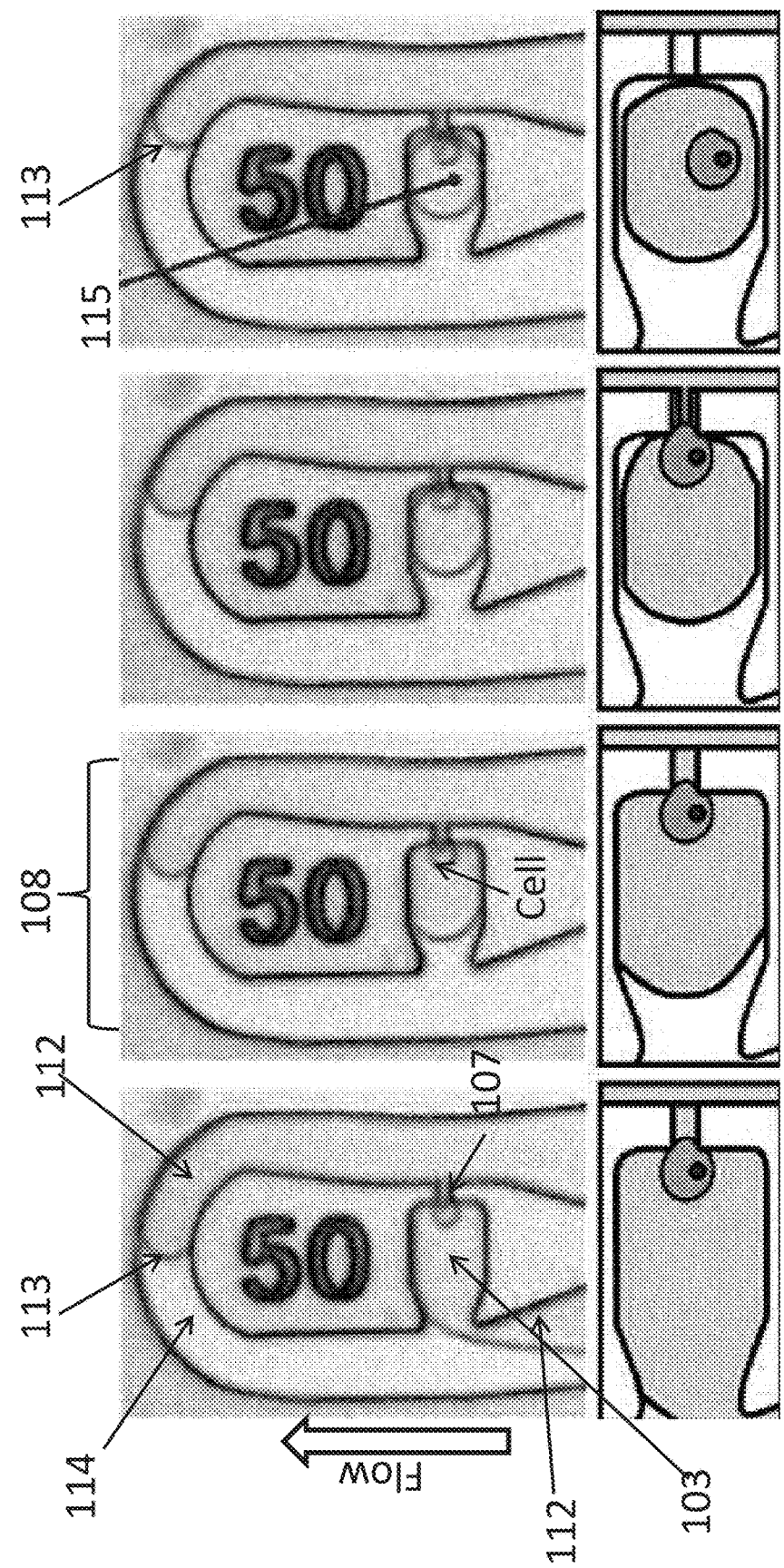
Figures 6C, 6D:
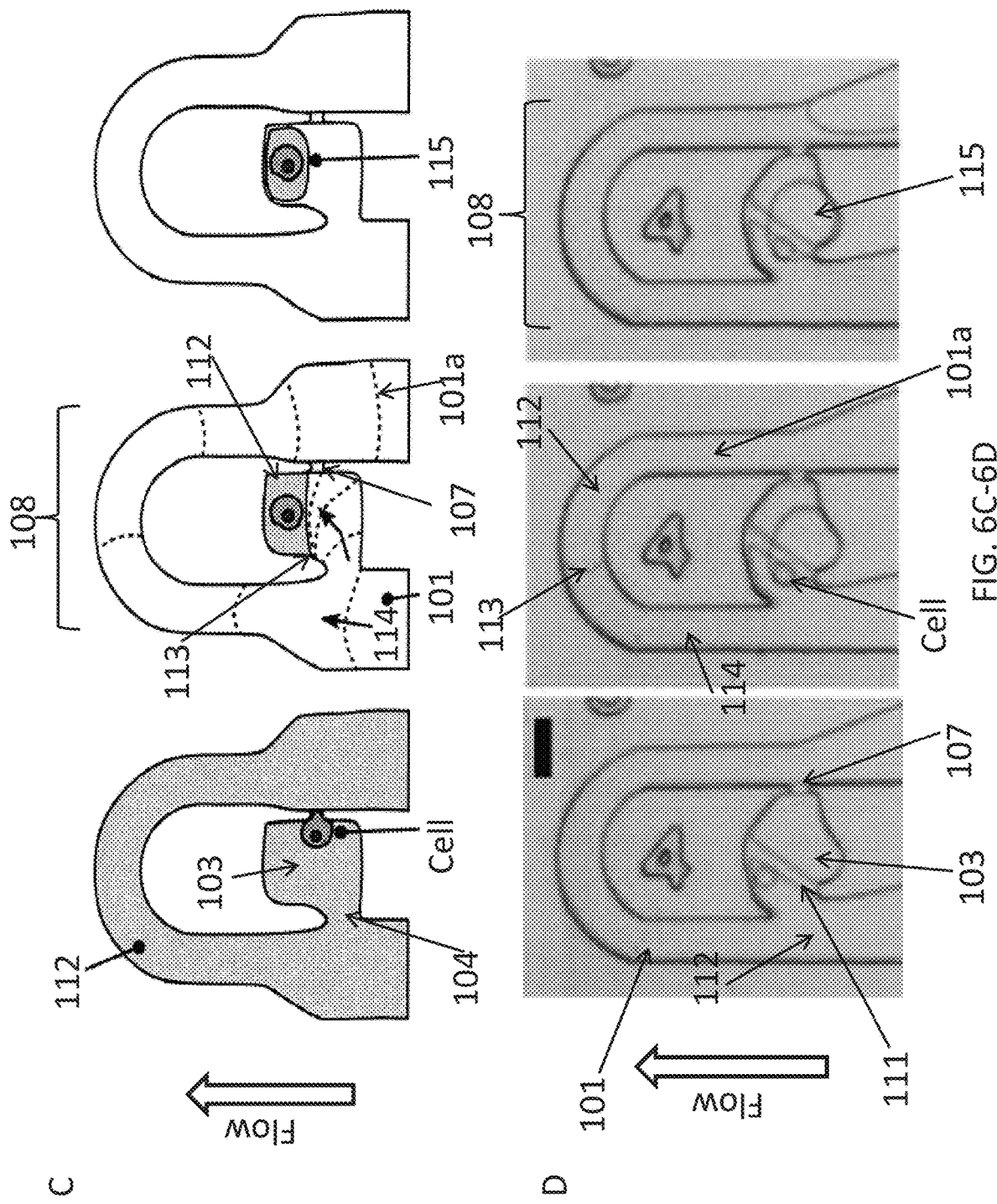
Figure 6E:
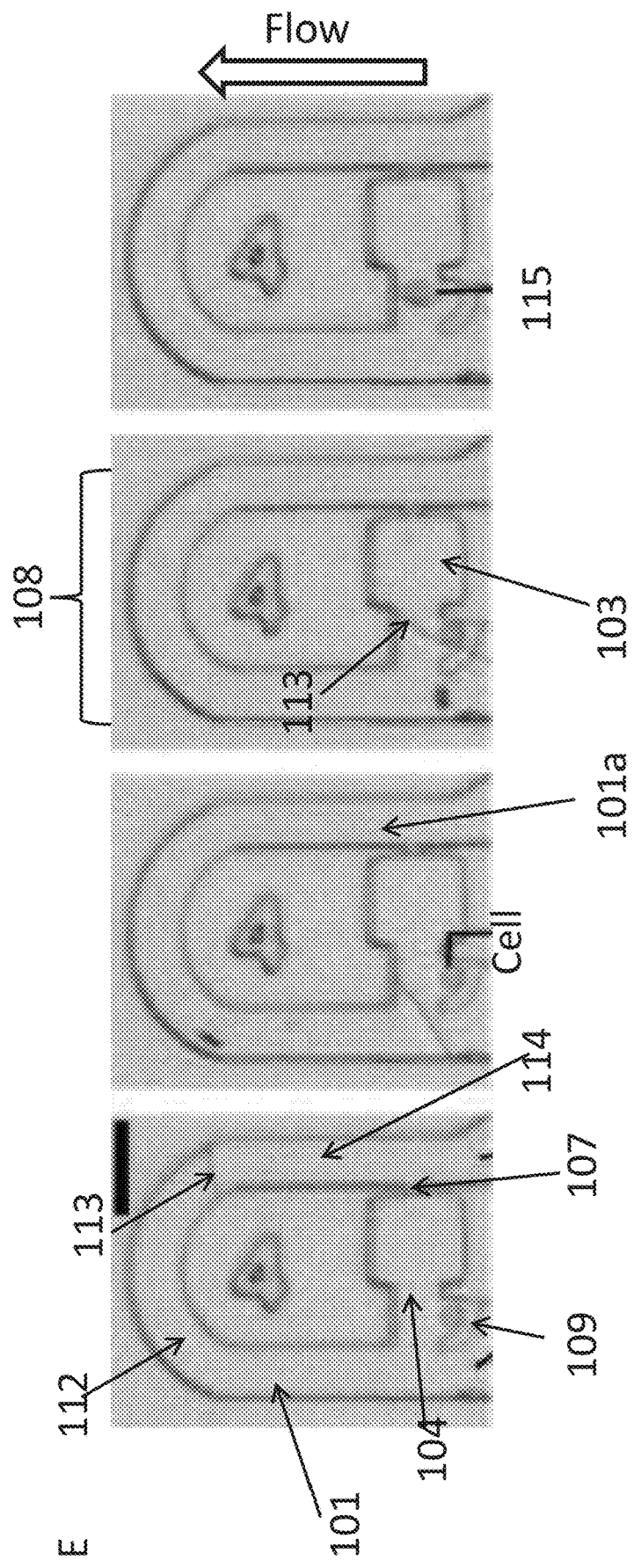

In one embodiment, a pressure is applied to the microfluidic device so that the second solution flows in a direction opposite to that of the first solution. Here, encapsulation of a single cell or particle in an aqueous droplet is based on "capillary valving". See H. Boukellal et al. *Lab Chip*, (2009) 9, 331-338. Here, the interface will preferably follow the path with the larger cross-section when flowing a reduced flow rate (i.e., less than 6 µl/hr, less than 2 µl/hr, or less than 0.1 µl/hr and 1 µl/hr). Further, in specific embodiments, the second solution is flowed through the microfluidic device in the absence of a surfactant to reduce wetting. As shown in FIG. 6E, when a cell or particle is trapped using the microfluidic device of FIG. 3B and the method set forth in FIG. 5E capillary valving will force the second solution to flow downstream past the trapping channel (107) toward the bypass channel (108). As the second solution flows past the trapping channel (107) the cell or particle will be released from the second opening (106) in the trapping chamber where it was plugged into the trapping chamber where it will be captured by the capture element (109) and retained within the trapping chamber. Then, as the interface (113) progresses into the microfluidic channel toward the first opening (104) in the trapping chamber (103) an interface (113) at the first opening (104) in the trapping chamber (103) is formed, causing a droplet (115) encapsulating the trapped cell or particle to form having the same dimensions of the trapping chamber (103).

In some embodiments, the single cell or particle containing droplets formed by any one of the encapsulation steps above, can be isolated (i.e., retrieved). In one embodiment, after encapsulation the flow of the second solution (e.g., oil) is reversed. For example, the second solution can be reversed by applying a pressure through a port that is opposite to the direction that the second solution first flowed through the microfluidic device. During this isolation step, the flow rate of the second solution is incrementally increased to 40 µl/h to displace the droplets from the trapping chamber(s). In embodiments whereby several droplets were formed sequentially, the droplet closest to the port is dislodged first and the reversed flow will sequentially displace the remaining droplets until all droplets are flowing through adjacent microfluidic channels of a microfluidic device, where they can be retrieved through a second port (output port) located downstream of the final trapping chamber in a series of trapping chambers. See FIG. 7. In another embodiment, a droplet encapsulating a single cell may be isolated by evicting the droplet from a trapping chamber by applying a positive pressure to a pressurized control channel located on the outermost surface of the trapping chamber (see FIG. 3C). Here, the pressurized control channel is kept at atmospheric pressure until after encapsulation, then the pressurized control channel is put under pressure. Increasing the pressure in the pressurized control channel exerts a force on the walls of the trapping chamber, which reduces the volume of the chamber, forcing the droplet out of the first opening in the trapping chamber into a microfluidic channel where it can be isolated as set forth above.

While the present invention has been shown and described with reference to certain embodiments thereof, it will be understood by those skilled in the art that various changes in from and details may be made therein without departing from the spirit and scope of the present invention, the non-limiting examples to follow and equivalents thereof.

EXAMPLES

Example 1: Device Configuration for Trapping Cells with High Efficiency

As stated above, the configuration of the bypass channel (108) is integral to accomplish efficient trapping and single-cell encapsulation. The bypass was shorted when compared to those known in the art. A cell proceeds through microfluidic channel (101) into the trapping chamber when its center of mass is located within the streamlines that flow down a microfluidic channel over the displacement elements and through a trapping chamber. As the incoming cells are distributed randomly across the cross-section of the channel, the probability of cell capture using one of the above referenced trapping methods is increased by increasing the ratio of the flow through the microfluidic channel over the flow through the bypass channel (Qtrap/Qbypass). Here, a particle (i.e., a cell) is preferentially directed towards a vacant trapping chamber if and only if Qtrap>Qbypass. However, increasing the hydrodynamic resistance of the bypass channel by using a lengthy channel causes the following issues: (1) cell clogging due to a limited shear rate through the bypass channel; (2) high pressure differential exerted on the captured cells; and (3) multiple cells captured per trapping chamber. Notably, a long bypass channel is not always compatible with a reliable encapsulation as captured cells tend to be squeezed out due to an excessive pressure differential.

Displacement elements are utilized to focus cells towards the capturing streamlines and make single-cell capture compatible with the subsequent encapsulation. See FIGS. 2A-2E. Displacement elements coerce cells into crossing streamlines to ensure capture regardless of their initial position. FIG. 2E. Here, it was shown that fluid flow is locally split between the diverted flow going under the displacement element (approximately 30% of the total flow) and the steering flow in the open microfluidic channel. The diverted flow is inaccessible to the typical cell, as the channel height between the channel sidewall and the maximum height of the displacement element is about 12 µm. Thus, a cell following a streamline heading under the overhang is displaced towards a steering flow streamline by sliding against the edge of the overhang.

Data revealed that a single displacement element elicits a weaker flow displacement than the series of six structures aligned in series. This is supported by numerical simulations that show the generation of an elongated longitudinal vortex by repeated structures (data not shown). Here, flow streamlines initially going below the overhangs (diverted flow) are steered towards the open microfluidic channel section (steering flow) after passing underneath 2 or more displacement elements. Consequently, a series of overhangs leads to improved cell focusing. As shown in FIG. 2E, the normalized lateral position $\gamma$ is used to monitor the position of the cell. Plotting the final lateral position $\gamma_f$ as a function of the initial cell position $\gamma_i$, shows that the overhangs displace cells towards the trapping chamber. Optimally, the series of overhangs are slanted compared to the walls of the channel (tapered) to gradually increase the portion of flow going under the structures and minimize the number of constrictions with higher shear stress. FIGS. 2A and 2C.

In embodiments that depend on cell plugging to trap a cell in a trapping chamber, complete plugging of the trapping channel by a cell: (1) prevents the capture of multiple cells per trap, and (2) enables cell-plugging encapsulation methods. Here, trapping channels with a square cross-section ensure an efficient plugging of the flow by single-cells, as shown in FIG. 4. This device design assures that an efficient plugging can be achieved with cells of different sizes and rigidity, as demonstrated by the observed ability to use both live and fixed cells. It also reduces the likelihood of the cell being deformed and forced through the trapping channel.

Further, the number of trapping chambers necessary to capture each cell in a sample of cells was evaluated in order to determine trapping efficiency. A498 cancer cells (~105 cells/mL) were injected using a syringe pump at low flow rate (6 to 20 µL/h) into a circuit primed with a 2% weight Pluronic F-68 solution in D-PBS (solution 1). Cell were monitored as they progressed through the microfluidic device, and the trapping events were recorded at the first vacant trapping chamber. Data (n=566 cells) revealed that an incoming cell is captured by the first unoccupied trapping chamber in 93.8% of cases, and by the second empty trapping chamber in a series of trapping chambers 5.6% of the time. Furthermore, a cell was not captured by one of the first 4 trapping chambers in a series of trapping chambers in less than 0.6% of trials. As such, the microfluidic devices of the present disclosure are self-correcting because a cell not captured by the first trapping chamber in a series of trapping chambers will be displaced towards a subsequent trapping chamber by the displacement elements where they will be captured.

In addition, we observed that using the subject methods and microfluidic devices, single-cell capture was equally efficient for live and fixed cells. For example, a single cell is captured in more than 96% of the cases for live cells, and 99% for fixed cells.

In view of the foregoing, by focusing cells towards the trapping chambers using the Qtrap>Qbypass design rule improved single-cell trapping efficiency using a short bypassing channel (Qtrap/Qbypass=0.2) compatible with the encapsulation step was achieved. Therefore, using the present methods and microfluidic devices a cell-of-interest is highly likely (>99%) to be trapped within the first two trapping chambers in a series of trapping chambers, ensuring that any sample of live or fixed single-cells injected in our device can be reliably trapped without cell loss, overcoming a major limitation of current single-cell droplet microfluidic encapsulation methods.

Example 2: Materials and Methods

Microfluidic devices were fabricated following typical protocols, such as those set forth in E. Brouzes, *Single-Cell Analysis: Methods and Protocols* (2012) pp. 105-139, the entire contents of which is incorporated herein by reference. Designs were created on Autocad 2000, printed onto Fuji transparent masks at 25,400 dpi (CAD/Art Services, Inc., OR). A photoresist mold was fabricated on a 3-inch silicon wafer (UniversityWafer, MA) using two-step photolithography. The first layer of negative photoresist (SU8-2010, MicroChem, MA) was about 12 µm thick, and the second layer (20 µm thick) was obtained after finely aligning the second mask to overlap with the design of the first one. The master was treated with a vapor of a fluorinated 1H, 1H, 2H, 2H-Perfluorooctyltrichlorosilane (007146, Oakwood Chemical, SC) for 90 minutes. A single layer of PDMS (Sylgard 184 Silicone Elastomer Kit, Dow Corning) obtained by molding, was bonded using an $O_2$ plasma cleaner (Harrick plasma), onto a glass slide previously spin-coated with PDMS (1,000 rpm for 40 seconds). This ensured comparable surface properties on the four walls of our circuit.

Surface treatment. A hydrophobic and fluorophilic device are required to obtain the exceptional results described above. As such, a solution of Novec $1720^2$ (3M™) was injected for 20 minutes at 100 µl/h just after bonding; then the chip is left to dry at room temperature for 20 minutes, before being placed on a hotplate at 150° C. for 30 minutes. This treatment protocol reliably provided high-quality surface treatment, displaying a static contact angle with purified water of $\theta_{static}=106°+/-3$ (n=16). The resulting microfluidic device is reusable by washing the elements with FC40 fluorinated oil and then placing it onto a hot plate at 100° C. for a at least 2 hours in the absence of water.

Microfluidic device operation. Fluorinated oil, HFE 7500 (3M™), was combined with a peg-based krytox surfactant[3] at 2% weight to ensure reproducible droplet generation and stability while guaranteeing good wetting on the treated walls (where desired). The microfluidic device is placed on an inverted microscope (Diaphot-TMD, Nikon) and the fluid flow was observed using a 10× objective (Ph1 10/0.30 DL 160/0.17, Nikon) under bright-field illumination. A 1 ml Gastight syringe (Hamilton) driven by a 290N Nemesys syringe pump (Cetoni GmbH) delivered drove flow rate. Images were recorded using a CCD camera (XCD-V60, Sony).

Normalized lateral position of cells through the microfluidic device. A goal was to normalize the position of the center of the cell so that it is null when the cell is in contact with the sidewall of the microfluidic channel from which the displacement elements extend out into the channel, and equal to 1 when flowing up against the opposite sidewall on which a trapping chamber resides.

If r is the estimated cell radius, $y_c$ the position of the center of the cell and $w_{ch}$ the width of the channel, then the normalized lateral position of a cell (y) is defined by the formula:

$$y = \frac{y_c - r}{w_{ch} - 2r}$$

Cell culture and viability assay. Experiments were conducted to demonstrate that the trapping-encapsulation methods set forth herein have a marginal effect on cell viability. There, there was no positional trapping effect, as cell viability did not correlate with specific traps along the microfluidic device.

Here, A498 cells and HeLa cells were maintained in complete medium consisting of Eagle's Minimum Essential Medium (EMEM, Quality Biological) and DMEM (Gibco 11965092), respectively, supplemented with 10% fetal bovine serum (Corning) and 1% Penicillin-Streptomycin (Gibco 15140122) in a standard tissue culture incubator (HERACELL VIOS 160i) at 37° C. and 5% $CO2$.

For device loading, cells were washed with DPBS, after detachment from culture dishes with Accutase (Innovative Cell Technologies) and kept on ice until loading. Calcein AM (Molecular Probes C1430) and Sytox orange (Molecular Probes Si 1368) were used to quantify cell viability. Optimal concentrations were found to be 0.2 µM for both dyes. The Live-Dead assays were conducted on a Nikon Eclipse Ti-E, using excitation filters 395/25 and 545/30 and emission filters 460/50 and 620/60 for Calcein AM and Sytox Orange respectively. When both signals were visible, the cell was considered compromised.

Droplet volume estimate. The volume of a droplet was calculated immediately after generation by measuring and multiplying the droplet surface area by the height of the trapping chamber. With $S_{droplet}$, representing the droplet surface area, $h_{ch}$ indicating the height of the channel and $V_{droplet}$ being the estimated volume of the droplet the following formula was used to determine droplet volument:

$$V_{droplet} = h_{ch} \times S_{droplet}$$

Example 3. Trapping and Encapsulation of Single Cells Using Droplet Microfluidics Cells were first isolated and immobilized into individual traps, a series of which are used to create a linear array of hydrodynamic capturing sites. See FIGS. 1A-1F. Each trap consists of two flow paths the trapping pathway and the bypass pathway. The trapping pathway circumvents the bypass pathway by allowing the flow of solution through a trapping channel that connects a trapping chamber of a first microfluidic channel to a second adjacent microfluidic channel. See FIG. 4. The trapping channels were designed to have a constricted opening of sub-cellular dimensions.

In certain embodiments, an incoming cell progresses downstream through an unoccupied trapping chamber to the trapping channel until it blocks the entrance of the trapping channel. The cell then plugs the trapping flow path (cell-plugging effect) and further fluid flow is diverted through the bypass channel, effectively reconfiguring the local flow topology.

As set forth above, the bypass channel was shortened to make the trapping and encapsulation steps compatible, and overcame the loss of trapping efficiency by incorporating displacement elements that displace incoming cells towards the trapping chambers.

Next, the same cell-plugging principle was utilized to facilitate single-cell encapsulation methods using the present microfluidic devices. Here, the injected immiscible solution (oil) was diverted towards the bypass channel until it surrounded the trapping chamber containing a single-cell. See FIG. 6A. This lead to two different modes of encapsulation: the bypass mode and the wetting-driven mode. For both methods Droplet generation was sequential and took place at all occupied traps, resulting in true single-cell encapsulation. The encapsulated cells were recovered for further analysis by reversing the flow of oil. See FIG. 7.

Based on the fluid injection rate and the surface properties of the microfluidic device, cell-encapsulation methods were developed to take advantage of the cell-plugging effect. As set forth herein, a captured cell plugs the trapping channel, thus diverting the incoming flow towards the bypass pathway. The fluid (oil) first closes the chamber entry by forming an oil-water interface before progressing through the bypass channel. A droplet is not yet generated, but the aqueous flow is split: a small portion is stationary in the trapping chamber, while the rest travels downstream through the bypass channel.

In the bypass mode, the droplet is generated when the oil front progresses through the entire bypass channel and cuts off the side of the trapping channel opposite to the cell. FIG. 6A. Some secondary droplets may occasionally get generated during the process, but are rapidly evacuated by the flow of oil. A second exemplary mode of encapsulation is wetting-driven and encapsulation occurs when the oil wets the walls of the trapping chamber and cuts off the trapping channel from within the trapping chamber as shown in FIG. 6B. This mode of encapsulation is dependent on the development of a thin precursor film that develops ahead of the macroscopic wetting front and creeps along the walls of the trapping chamber until it reaches the trapping channel. The aqueous phase is thus surrounded by oil and a droplet is generated before the oil front can cut off the trapping channel from the bypass channel.

While both the bypass and wetting-driven methods of encapsulation resulted in the encapsulation of a single cell, their underlying principles are quite different. The wetting-driven mode depends on a series of quasi-equilibrium states, as a thin film of oil needs to develop along the trapping chamber walls. This implies a very slow inflow of oil and an excellent oil wetting of the channel surfaces. Bypass mode is less dependent on surface properties and is relatively accommodating of various flow rates. Importantly, a captured cell can be extruded through the trapping channel if the pressure differential it experiences reaches a critical value. Thus, it was necessary to design a short bypass channel with a large cross-section to minimize the pressure exerted on trapped cells when oil flows through a bypass channel.

A cell proceeds through the trapping pathway only if its center of mass is located within the streamlines that flow through the chamber. As the incoming cells are distributed randomly across the cross-section of the channel, one can increase the probability of cell capture by increasing the ratio of the flow through the trapping pathway over the flow through the bypassing channel ($Q_{trap}/Q_{bypass}$). It has been shown herein that a particle is preferentially directed towards a vacant trapping pathway if and only if $Q_{trap} > Q_{bypass}$. However, increasing the hydrodynamic resistance of the bypass channel by using a lengthy channel causes multiple problems: (1) cell clogging due to a limited shear rate through the bypassing pathway; (2) high pressure differential exerted on the captured cells; and (3) multiple particles per trap. Importantly, a long bypass channel is not compatible with a reliable encapsulation as captured cells tend to be squeezed out due to an excessive pressure differential.

To overcome these issues, the present microfluidic devices include a plurality of displacement elements to focus cells towards the capturing streamlines and make single-cell capture compatible with the subsequent encapsulation. FIG. 2A-2E. Here, tapered displacement elements coerce cells into crossing streamlines to ensure capture regardless of their initial position. Streamlines initially going below the displacement elements (diverted flow) are steered towards the open channel section (steering flow) after passing underneath at least two displacement elements. Consequently, a series of displacement elements exhibited better cell focusing characteristics.

Figure 2D:
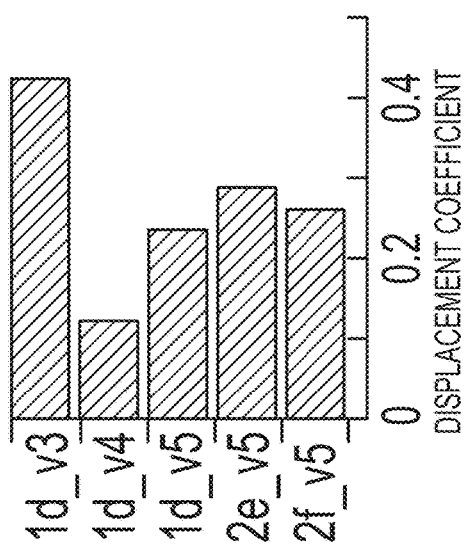
Figure 2E:
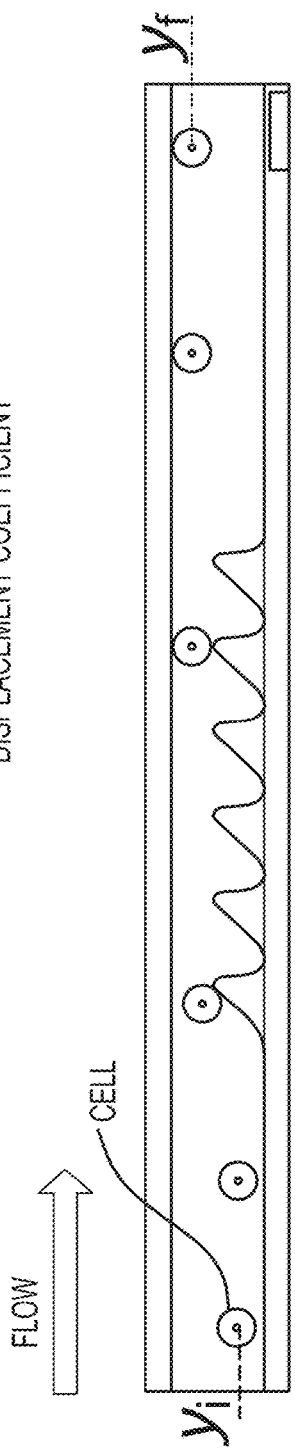

The effect of the displacement elements were examined by reporting the lateral position of cells flowing through a straight microfluidic channel comprising a series of displacement elements FIG. 2C-2E. The normalized lateral position γ is used to monitor the position of the cell (ESI). Plotting the final lateral position yf as a function of the initial cell position yi, shows that the displacement elements efficiently displace cells.

From the point of view of rare samples, it was critical to evaluate the percentage of single cells that can be effectively trapped and further analyzed. Thus, the number of traps necessary to capture each cell was determined in order to define the trapping efficiency of the present methods and devices. As set forth above cells were injected through a port into a microfluidic channel. Here, A498 cancer cells (~105 cells/ml) were injected using a syringe pump at low flow rate (6 to 20 µl/h) into a circuit primed with a 2% weight Pluronic F-68 solution in D-PBS. Cells were monitored as they progress through the channels and trapping chamber, and the trapping events recorded. Cell capture was equally efficient for live and fixed cells. Aggregates of live cells are occasionally injected into the circuit, which result in multiple cells being trapped in a single capturing site. Nevertheless, a single cell is captured in more than 96% of the cases for live cells, while this rate reaches 99% for fixed cells.

By focusing incoming cells towards the trapping pathway, the Qtrap>Qbypass design rule is fundamentally amended and as a result a very high single-cell trapping efficiency using a short bypassing channel (Qtrap/Qbypass=0.2) was obtained.

The distributions of droplet volume for both live and fixed cells are unimodal and were left-skewed. Most droplets follow a normal distribution: 90% of the droplets have a volume of 164±9 pl for live cells; 85% of the droplets fall within the 155±8 pl range for fixed cells. Both distributions are centered on the estimated volume of the trapping chamber (i.e., 160 pl). The smaller droplets result from a leaking flow through the trapping channel when cells do not completely plug the flow through the trapping channel. This effect was also observed for very rigid particles such as strongly fixed cells or polystyrene beads (data not shown). The droplet content reflects the cell distribution during the trapping step, and most droplets contain a single cell.

Figure 7:
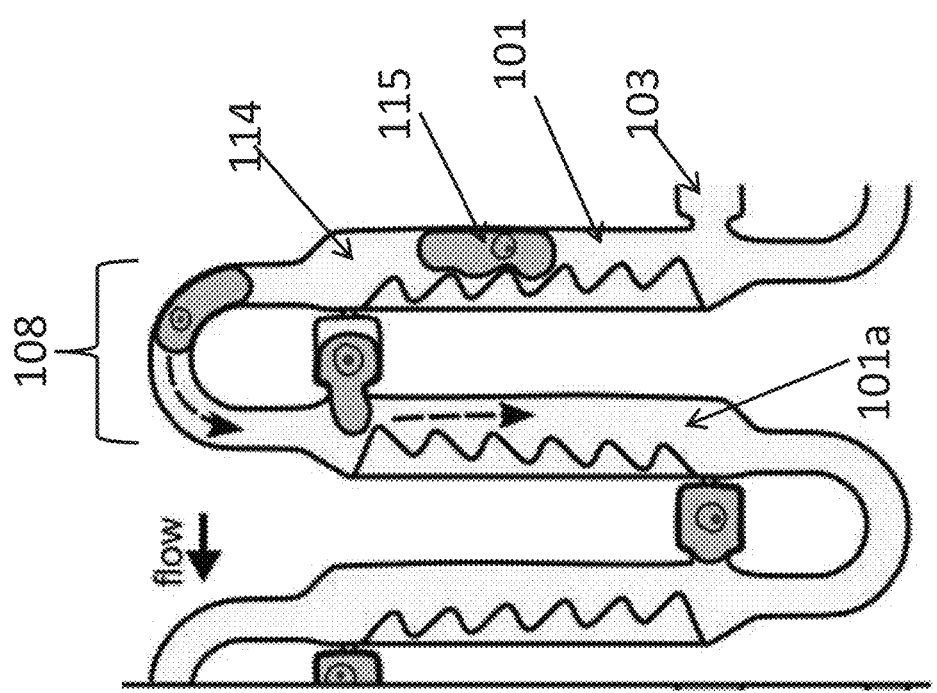
FIG. 7. An exemplary embodiment, whereby a droplet is isolated using a microfluidic device and method of the present disclosure.

Once the encapsulation was completed, single cells were retrieved by reversing the flow of oil (FIG. 7). This was achieved by slowly reducing the flow of incoming oil, unplugging the oil tubing and connecting another oil tubing into the outlet. The oil flow rate is incrementally increased to 40 µl/h to displace the droplets out of the traps. The droplet closest to the outlet is dislodged first and sequentially triggers the displacement of the other droplets while traveling through the circuit. At the level of a single module, the presence of a droplet in the bypass channel increases its effective hydrodynamic resistance and thus slightly increases the pressure differential across the trapping chamber. This pressure imbalance was sufficient to dislodge the trapped droplet. As such, the present devices and methods permit the isolation of single-cell containing droplets from a larger sample of cells. FIG. 7. These single-cells encapsulated within droplets can therefore be retrieved and further evaluated using methods known by those of ordinary skill in the art.

What is claimed is:

1. A microfluidic device comprising:
    a first region comprising
        a microfluidic channel, wherein said microfluidic channel comprises at least one displacement element on a first inner sidewall surface of said microfluidic channel, wherein said at least one displacement element extends into the microfluidic channel toward an second inner sidewall surface of the microfluidic channel that is opposite said first inner sidewall surface, and
        at least one trapping chamber coupled to the microfluidic channel downstream of said at least one displacement element, wherein said at least one trapping chamber comprises a first opening in said second inner sidewall of said microfluidic channel that allows the flow of fluid into said at least one trapping chamber;
    a second region downstream of said first region comprising a second microfluidic channel; and
    a third region comprising a bypass channel, wherein said bypass channel adjoins the first region and the second region.

2. The microfluidic device of claim 1, further comprising a port in a sidewall of said microfluidic channel, wherein said port is located upstream of said at least one displacement element.

3. The microfluidic device of claim 1, wherein said at least one displacement element comprises between three and nine tapered displacement elements, wherein each of said tapered displacement elements are aligned in series on said first inner sidewall surface of said microfluidic channel.

4. The microfluidic device of claim 3, comprising six tapered displacement elements.

5. The microfluidic device of claim 3, wherein each of said tapered displacement elements has a maximum height of between 10 μm and 25 μm, and wherein the maximum height of the microfluidic channel is between 22 μm and 37 μm.

6. The microfluidic device of claim 5, wherein each of said tapered displacement elements, from upstream to downstream, have a greater maximum height than each preceding tapered displacement element in the series of displacement elements.

7. The microfluidic device of claim 3, wherein said at least one trapping chamber comprises at least two parallel sidewalls.

8. The microfluidic device of claim 3, wherein said at least one trapping chamber is enclosed except for said first opening.

9. The microfluidic device of claim 8, further comprising a pressurized control channel on an outermost surface of said at least one trapping chamber.

10. The microfluidic device of claim 9, further comprising a capture element located downstream of said first opening, wherein said capture element is located on a sidewall of said microfluidic channel, and wherein said capture element extends into said first opening of the trapping chamber and a portion of said microfluidic channel.

11. The microfluidic device of claim 10, wherein said capture element is hook-shaped.

12. The microfluidic device of claim 7, wherein said at least one trapping chamber comprises a second opening opposite said first opening, and wherein said second opening is connected to a trapping channel.

13. The microfluidic device of claim 12, wherein said trapping channel has a cross sectional height and width that does not permit a cell having a diameter of between 10 μm and 26 μm to traverse the at least one trapping channel.

14. The microfluidic device of claim 13, further comprising a capture element located on a sidewall of said microfluidic channel, and wherein said capture element extends into said first opening of the at least one trapping chamber and a portion of said microfluidic channel.

15. The microfluidic device of claim 14, wherein said capture element is downstream of said first opening of said at least one trapping chamber.

16. The microfluidic device of claim 14, wherein said capture element is upstream of said first opening of said at least one trapping chamber.

17. The microfluidic device of claim 12, further comprising a blocking rail within said at least one trapping chamber, wherein said blocking rail permits the flow of fluid through said at least one trapping chamber.

18. The microfluidic device of claim 12, wherein said bypass channel is a U-shaped channel in fluid communication with said first region and said second region.

19. The microfluidic device of claim 18, wherein said trapping channel connects said first microfluidic channel and said second microfluidic channel, and wherein said first microfluidic channel and said second microfluidic channel are in fluid communication.

* * * * *